(12) United States Patent
Senanayake et al.

(10) Patent No.: US 6,780,891 B2
(45) Date of Patent: Aug. 24, 2004

(54) TRAMADOL ANALOGS AND USES THEREOF

(75) Inventors: Chris Hugh Senanayake, Shrewsbury, MA (US); Thomas P. Jerussi, Framingham, MA (US); Paul T. Grover, Franklin, MA (US); Qun Kevin Fang, Wellesly, MA (US); Mark Currie, Sterling, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 10/308,878

(22) Filed: Dec. 2, 2002

(65) Prior Publication Data

US 2003/0171440 A1 Sep. 11, 2003

Related U.S. Application Data

(60) Provisional application No. 60/335,275, filed on Nov. 30, 2001.

(51) Int. Cl.[7] .................... C07C 211/01; A01N 33/04; A61K 31/135
(52) U.S. Cl. ...................... 514/646; 564/305; 564/339; 564/440
(58) Field of Search ................ 564/305, 339, 564/440; 514/646

(56) References Cited

U.S. PATENT DOCUMENTS

| | | | |
|---|---|---|---|
| 3,652,589 A | 3/1972 | Flick et al. | 260/326.5 M |
| 5,223,541 A | 6/1993 | Maryanoff et al. | 514/644 |
| 5,414,129 A | 5/1995 | Cherkez et al. | 564/425 |
| 5,468,744 A | 11/1995 | Raffa et al. | 514/282 |
| 5,672,755 A | 9/1997 | Lerman et al. | 564/425 |
| 5,723,668 A | 3/1998 | Buschmann et al. | 564/304 |
| 5,728,885 A | 3/1998 | Buschmann et al. | 564/304 |
| 6,017,963 A | 1/2000 | Alfonso et al. | 514/646 |
| 6,056,968 A | 5/2000 | Gilbert et al. | 424/422 |

FOREIGN PATENT DOCUMENTS

| | | |
|---|---|---|
| GB | 997399 | 7/1965 |
| WO | WO 00/32554 | 6/2000 |
| WO | WO 00/32558 | 6/2000 |
| WO | WO 00/51685 | 9/2000 |
| WO | WO 01/34125 A2 | 5/2001 |

OTHER PUBLICATIONS

Bamigbade et al., *British J. Anaesthesia*, 1997: 79(3): pp 352–356.
Bamigbade et al., *Pain Reviews*, 1998; 5: pp 155–182.
Buccellati et al., *European J. Pain*, 2000; 4: pp 413–415.
Frink et al., *Arzneimittel–Forschung/Drug Research*, 1996; 46(11); pp 1029–1036.
Garrido et al, *Journal of Pharmacology & Experimental Thereapeuctics*, 2000, vol. 295, No. 1, pp. 352–359.
Gillen et al., *Naunyn–Schmiedeberg's Arch Pharmacol*, 2000; 362; pp 116–221 362.
Gillen et al., *Society for Neuroscience*, 1999 vol. 25, p. 1706.
Ground et al., *British Journal of Clinical Pharmacology*, 1999; 48(2); pp. 254–257.
Halfpenny et al., *British J. of Anaesthesia*, 1999; 83: pp. 909–915.
Lai et al., *European J. Pharmacol*, 1996; 316, pp 369–372.
Parr et al., *Eur J. Clin Pharmacol*, 1997; 53(3–4); pp 235–239.
Poulsen et al., *Clin Pharmacol & Therapeutics*, 1996; 60(6); pp 636–644.
Potschka et al., *British J. Pharmacol*, 2000; 131, pp 203–212.
Raffa et al., *J. Pharmacol. & Experimental Therapeutics*, 1996; 278(3), pp 1098–1104.
Raffa et al., *J. Pharmacol. & Experimental Therapeutics*, 1992; 260(1), pp 275–285.
Rojas–Corrales et al., *Life Sciences*, 1998; vol. 63, No. 12, pp. PL 175–180.
Sacerdote et al., *Intl. J. Immunopharmacology*, 1999; 21, pp. 727–734.
Shipton, E.A., *Anaesth Intensive Care*, 2000; 28, pp. 363–374.
Sindrup et al., *Clinical Pharmacology & Therapeutics*, 1999; vol. 66, No. 6, pp. 636–664.
Valle et al., *J. Pharmacology & Experimental Therapeutics*, 2000; 293: pp. 646–653.
Wilder–Smith et al., *Anesthesiology*, 1999; vol. 91, No. 3A, pp. A1004.

Primary Examiner—Brian Davis
(74) Attorney, Agent, or Firm—Heslin Rothenberg Farley & Mesiti P.C.; Mary Louise Gioeni, Esq.

(57) ABSTRACT

Compounds of formula I are effective in treating disorders modulated by opiate receptor activity and/or monoamine activity.

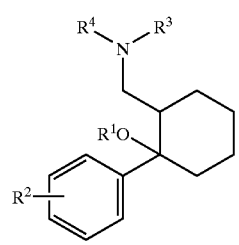

I

In formula I, $R^1$ is selected from alkyl, aryl, alkylaryl, substituted alkyl, substituted aryl, and substituted alkylaryl; $R^2$ is selected from hydrogen, hydroxy, cyano, haloalkyl, glycosyl, $SO_2R^5$, and $OR^5$; $R^3$ and $R^4$ are independently selected from hydrogen and lower alkyl, or $R^3$ and $R^4$ taken together with nitrogen form a five- or six-membered heterocyclic or substituted heterocyclic ring; and $R^5$ is selected from alkyl, aryl, alkylaryl, substituted alkyl, substituted aryl, and substituted alkylaryl.

61 Claims, No Drawings

TRAMADOL ANALOGS AND USES THEREOF

CROSS REFERENCE TO RELATED APPLICATIONS

This application claims priority from U.S. provisional application, serial No. 60/335,275, filed Nov. 30, 2001, the entire disclosure of which is incorporated herein by reference.

FIELD OF THE INVENTION

The invention relates to tramadol analogs that are useful for the treatment of CNS-related disorders including pain, anxiety, depression and attention deficit disorder.

BACKGROUND OF THE INVENTION

Opioids such as morphine are very effective for the treatment of pain, but can result in very serious adverse effects, including respiratory depression, and addiction and dependency. Less serious side effects include gastrointestinal inhibition effects and obstipation. As a result, the use of such drugs is limited by the possibility of adverse effects. There is, therefore, a need for effective analgesics, which are not associated with these adverse effects.

U.S. Pat. No. 3,652,589, to Flick, discloses a genus of phenol ethers, which are described as having analgesic properties. The genus includes 2-((dimethylamino)methyl)-1-(3-methoxyphenyl)-cyclohexanol), which has been given the name tramadol. The patent also discloses 3-benzyloxyphenyl analogues of tramadol. U.S. Pat. No. 5,733,936 discloses tramadol analogs substituted at the 4-position of the cyclohexane ring.

Tramadol is commercially available from Ortho-McNeil Pharmaceuticals as a racemic mixture of the (R,R)- and (S,S)-enantiomers under the trademark ULTRAM®. It is approved by the United States Food and Drug Administration for treatment of pain, and reportedly does not produce the side effects generally associated with opioids. However, because tramadol is less effective in relieving pain than the opioid drugs, there remains a need for alternative analgesic compounds.

SUMMARY OF THE INVENTION

In one aspect, the invention relates to compounds of formula I:

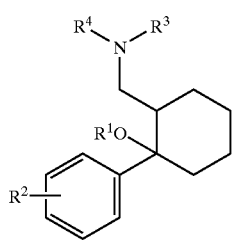

wherein
- $R^1$ is selected from alkyl, aryl, alkylaryl, substituted alkyl, substituted aryl, and substituted alkylaryl;
- $R^2$ is selected from hydrogen, hydroxy, cyano, haloalkyl, glycosyl, $SO_2R^5$, and $OR^5$;
- $R^3$ and $R^4$ are independently selected from hydrogen and lower alkyl, or $R^3$ and $R^4$ taken together with nitrogen form a five- or six-membered heterocyclic or substituted heterocyclic ring; and
- $R^5$ is selected from alkyl, aryl, alkylaryl, substituted alkyl, substituted aryl, and substituted alkylaryl.

It has been unexpectedly discovered that compounds of formula I possess unique pharmacological characteristics with respect to stimulation of opiate receptors and increasing monoamine levels, particularly by inhibition of norepinephrine transport. Therefore, these compounds are effective in treating disorders, including CNS-related disorders, modulated by opiate receptor activity and/or monoamine activity, with diminished side effects compared to administration of the current standards of treatment. These disorders include, but are not limited to, acute and chronic pain, affective disorders, including anxiety and depression, and attention deficit disorders.

In the context of the present invention, alkyl is intended to include linear, branched, or cyclic hydrocarbon structures and combinations thereof. Lower alkyl refers to alkyl groups of from 1 to 4 carbon atoms. Examples of lower alkyl groups include methyl, ethyl, propyl, isopropyl, butyl, s-and t-butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, and norbornyl Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxy-carbonyl, and benzyloxycarbonyl. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S; each of which rings is optionally substituted with 1–3 lower alkyl, substituted alkyl, substituted alkynyl, =O, —$NO_2$, halogen, hydroxy, alkoxy, $OCH(COOH)_2$, cyano, —$NR^1R^2$, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, alkoxy, cyano, phenyl, benzyl, benzyloxy, carboxamido, heteroaryl, heteroaryloxy, —$NO_2$ or —NRR (wherein R is independently H, lower alkyl or cycloalkyl, and —RR may be fused to form a cyclic ring with nitrogen); The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl.

Heteroarylalkyl means an alkyl residue attached to a heteroaryl ring. Examples include, e.g., pyridinylmethyl, and pyrimidinylethyl.

Heterocycle or heterocyclic means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, aryl, cycloalkyl, or heterocyclyl refer to alkyl, aryl, cycloalkyl, or heterocyclyl wherein up to three H atoms in each residue are replaced with alkyl, aryl, haloalkyl, halogen, hydroxy, loweralkoxy, carboxy, carboalkoxy, carboxamido, cyano, carbonyl, nitro, amino (primary, secondary or tertiary), alkylthio, sulfoxide, sulfone, acylamino, amidino, phenyl, benzyl, heteroaryl, phenoxy, benzyloxy, or heteroaryloxy, or substituted aryl, wherein up to three H atoms in each residue are replaced with alkyl, aryl, haloalkyl, halogen, hydroxy, loweralkoxy, carboxy, carboalkoxy, carboxamido, cyano, carbonyl, nitro, amino (primary, secondary or tertiary), alkylthio, sulfoxide, sulfone, acylamino, amidino, phenyl, benzyl, heteroaryl, phenoxy, benzyloxy, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$ Glycosyl means a sugar residue, attached through an ether linkage. Examples of glycosyl groups include glycosyl, fructosyl, mannosyl, and lactosyl.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

DETAILED DESCRIPTION OF THE INVENTION

The present invention relates to the genus of compounds of formula I:

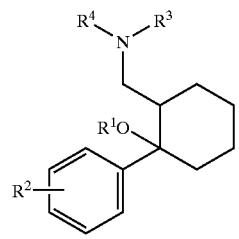

wherein $R^1$ is selected from alkyl, aryl, alkylaryl, substituted alkyl, substituted aryl, and substituted alkylaryl;

$R^2$ is selected from hydrogen, hydroxy, cyano, haloalkyl, glycosyl, $SO_2R^5$, and $OR^5$;

$R^3$ and $R^4$ are independently selected from hydrogen and lower alkyl, or $R^3$ and $R^4$ taken together with nitrogen form a five- or six-membered heterocyclic or substituted heterocyclic ring; and $R^5$ is selected from alkyl, aryl, alkylaryl, substituted alkyl, substituted aryl, and substituted alkylaryl.

Compounds of the genus may exist as a cis- or trans-isomer. In addition, each conformational isomer may exist as one of a pair of enantiomers because two chiral centers are present in the cyclohexane ring. Accordingly, each member of the genus includes two diasteromeric pairs or four individual enantiomers, designated (R,R)—, (S,S)—, (R,S)—, (S,R)—.

In one embodiment, the present invention relates to a subgenus of the compounds of formula I; the compounds of the subgenus have the structure of formula II:

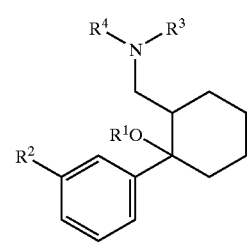

wherein $R^1$ is selected from alkyl, aryl, alkylaryl, substituted alkyl, substituted aryl, and substituted alkylaryl;

$R^2$ is hydrogen or $OR^1$; and $R^3$ and $R^4$ are independently selected from hydrogen and lower alkyl, or $R^3$ and $R^4$ taken together with the nitrogen atom form a five- or six-membered heterocyclic or substituted heterocyclic ring.

The present invention particularly relates to several individual compounds of formula I/II. In a first, hereinafter termed O-methyl tramadol (OMT), $R^1$, $R^3$, and $R^4$ are each methyl, and $R^2$ is methoxy. In a second, termed O-desmethyl O-methyl tramadol (ODMOMT), $R^1$, $R^3$, and $R^4$ are each methyl, and $R^2$ is hydroxy. The structures of OMT and ODMOMT are shown below, with tramadol and its O-desmethyl metabolite for comparison. The N-desmethyl analogs of these compounds, that is, where $R^1$ is methyl, $R^2$ is methoxy or OH, and either or both of $R^3$ or $R^4$ are hydrogen, are also of interest. OMT, ODMOMT and the N-desmethyl analogs include both cis- and trans-isomers, all four enantiomers ((R,R)—, (S,S)—, (R,S)—, and (S,R)—) racemic mixtures thereof and racemic mixtures enriched to any degree in an enantiomer.

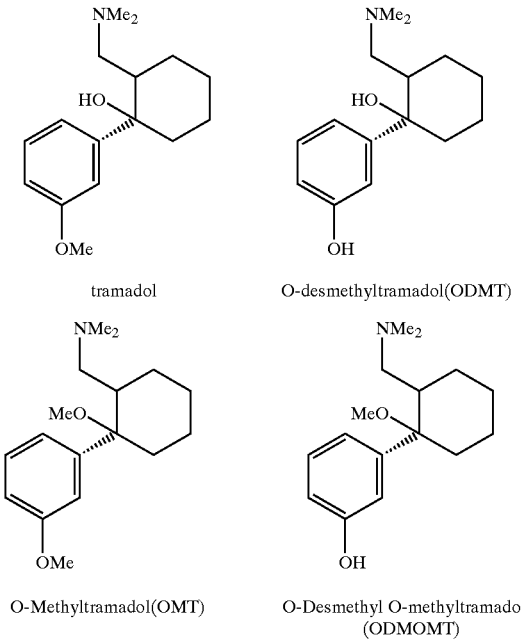

tramadol

O-desmethyltramadol(ODMT)

O-Methyltramadol(OMT)

O-Desmethyl O-methyltramadol (ODMOMT)

Other specific compounds of formula I that are of particular interest include the following.

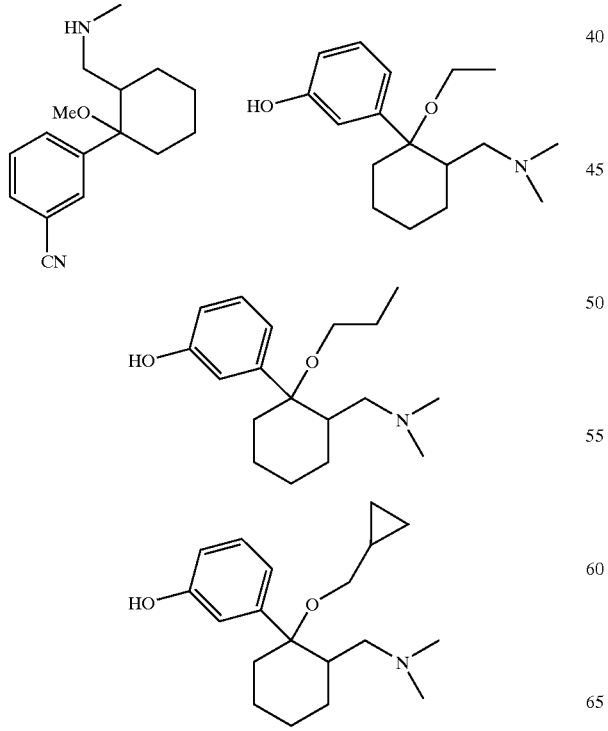

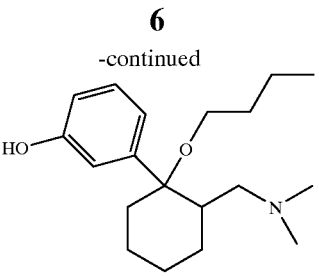

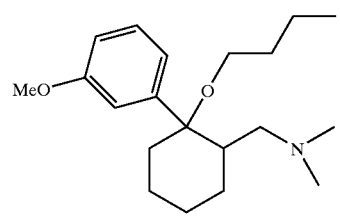

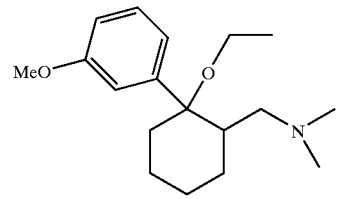

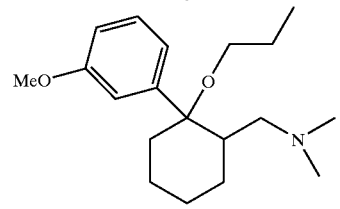

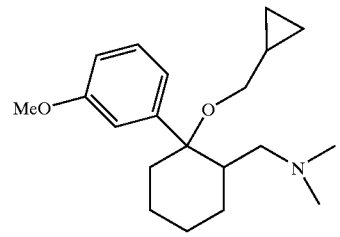

Compounds of formula I are useful for treating disorders modulated by opiate receptor activity and/or monoamine activity. Accordingly, the present invention relates to a method for such treatment, comprising administering to a mammal in need thereof a therapeutically effective amount of a compound of formula I, or a pharmaceutically acceptable salt thereof. In particular, the compound of formula I may be O-methyl tramadol or O-desmethyl O-methyl tramadol. As used herein, the term disorder modulated by opiate receptor activity and/or monoamine activity refers to a disorder, disease or condition opiate receptor activity and/or monoamine activity is an effective means of alleviating the disorder or one or more of the biological manifestations of the disease or disorder; or interferes with one or more points in the biological cascade leading to the disorder or responsible for the underlying disorder; or alleviates one or more symptoms of the disorder. Thus, disorders subject to modulation include those for which:

the lack of opiate receptor activity and/or monoamine activity is a cause of the disorder or one or more of the biological manifestations, whether the activity was altered genetically, by infection, by irritation, by internal stimulus or by some other cause;

the disease or disorder or the observable manifestation or manifestations of the disease or disorder are alleviated by opiate receptor activity and/or monoamine activity. The lack of opiate receptor activity and/or monoamine activity need not be causally related to the disease or disorder or the observable manifestations thereof; and/or opiate receptor activity and/or monoamine activity interferes with part of the biochemical or cellular cascade that results in or relates to the disease or disorder. In this respect, the opiate receptor activity and/or monoamine activity alters the cascade, and thus controls the disease, condition or disorder.

Disorders modulated by opiate receptor activity and/or monoamine activity include acute and chronic pain, affective disorders, including depression and anxiety, behavioral disorders, including attention deficit disorders, eating disorders, cerebral function disorders, substance abuse, sexual dysfunction, and urinary incontinence.

As noted above, it has been found that compounds of formula I, particularly OMT, ODMOMT, and their N-desmethyl analogs are effective analgesics. The compounds provide relief of chronic and acute pain while avoiding the side effects associated with opioid drugs, particularly respiratory depression. Accordingly, the present invention also relates to a method for relieving acute and chronic pain. The method comprises administering to a mammal in need thereof a therapeutically effective amount of a compound of formula I or of a pharmaceutically acceptable salt thereof. In particular, OMT and/or ODMOMT may be administered.

It has also been found that compounds of formula I are effective for the treatment of affective disorders. Affective disorders are defined as a group of disorders characterized by a disturbance of mood, accompanied by a full or partial manic or depressive symptom. (*Tabor's Medical Dictionary*) The group includes, but is not limited to depression, anxiety disorders, bipolar disorder, chronic fatigue disorder, seasonal affective disorder, premenstrual syndrome, perimenopause, menopause and male menopause. Depression is characterized by changes in mood, and by feelings of intense sadness or pessimistic worry. Symptoms include insomnia, anorexia, mental slowing and loss of drive, enthusiasm, and libido. These disorders are additionally characterized in that increasing monoamine levels, especially norepinephrine, reduces symptoms. Accordingly, the present invention also relates to a method for treating affective disorders, including depression. The method comprises administering to a mammal in need thereof a therapeutically effective amount of a compound of formula I, or a pharmaceutically acceptable salt thereof.

The compounds of formula I are also effective for treating behavioral disorders, which are defined as disorders affecting one's behavior resulting in inappropriate actions in learning and social situations. Behavioral disorders include attention deficit disorder (ADD). The term ADD, as used herein, includes both attention deficit disorder and attention deficit disorder with hyperactivity (ADHD), and is used in accordance with its accepted meaning in the art. (See, for example, *Diagnostic and Statistical Manual of Mental Disorders*, Revised, Fourth Ed., (DSM-III-R), American Psychiatric Assocation, 1997.) As used herein, the term attention deficit disorder includes disruptive behavior disorder as characterized in DSM-IV-R as categories 314.xx (including 314.01, 314.00 and 314.9), 312.xx and 313.xx. The skilled artisan will recognize that there are alternate nomenclatures, nosologies, and classification systems for pathological conditions and that these systems evolve with medical scientific progress. Methylphenidate (RITALIN®) is typically the drug of choice for the treatment and/or prevention of ADD. Dextroamphetamine, tricyclic antidepressants, for example, imipramine, caffeine, and other psychostimulants such as pemoline and deanol, are less preferred alternatives to methylphenidate. Common side effects of methylphenidate include sleep disturbances, including insomnia, depression or sadness, headache, stomachache, suppression of appetite, elevated blood pressure, and, with large continuous doses, a reduction of growth. Accordingly, alternate means of treating or preventing attention deficit disorders would be of great benefit.

The compounds of formula I are also effective for treating eating disorders. Eating disorders are defined as a disorder of one's appetite or eating habits or of inappropriate somatotype visualization. Eating disorders include bulimia, anorexia, obesity and cachexia.

The compounds of formula I are also effective for treating cerebral function disorders. The term cerebral function disorder, as used herein, includes cerebral function disorders involving intellectual deficits such as senile dementia, Alzheimer's type dementia, memory loss, amnesia/amnestic syndrome, epilepsy, disturbances of consciousness, coma, lowering of attention, speech disorders, Parkinson's disease, Lennox syndrome, autism, hyperkinetic syndrome and schizophrenia. Also within the meaning of the term are disorders caused by cerebrovascular diseases including cerebral infarction, cerebral bleeding, cerbral arteriosclerosis, cerebral venous thrombosis, head injuries, and the like, where symptoms include disturbance of consciousness, senile dementia, coma, lowering of attention, and speech disorders.

The compounds of formula I are also effective for treating substance abuse. The term substance abuse includes addiction to cocaine, heroin, nocotine, alcohol, anxiolytic and hypnotic drugs, cannabis (marijuana), amphetamines, hallucinogens, phenylcyclidine, volatile solvents, and volatile nitrites. Nicotine addiction includes nicotine addiction of all known forms, such as smoking cigarettes, cigars and/or pipes, and addiction to chewing tobacco.

The compounds of formula I are also effective for treating sexual dysfunction (e.g., erectile dystunction and female sexual dysfunction). The term sexual dysfuntion, as used herein, encompases male sexual dysfunction, or erectile dysfunction, and female sexual dysfunction, including orgasmic dysfunction related to clitoral disturbances. The term erectile dysfunction as used herein means an inability to achieve penile erection or ejaculation or both, or an inability to obtain or sustain an erection adequate for intercourse. The relative activity, potency and specificity of a compound of formula I in the treatment of sexual dysfunction can be assessed by determination of an $IC_{50}$ value, as described in U.S. Pat. No. 5,656,629. Briefly, the cGMP-PDE and other PDE isozymes are isolated from cardiovascular tissues (heart and aorta) of various animal species and man by anion-exchange and affinity chromatography as described by Silver et al., *Sec. Messeng. Phos.*, 13: 13–25 (1991) PDE activity, in the presence and absence of test compounds is determined essentially as described by Thompson et al., *Adv. Cyclic Nucleotide Res.*, 10:69–92. To determine the potency and selectivity of compounds as PDE inhibitors, compounds are screened for their effect on cyclic nucleotide hydrolysis at 10 $\mu$M. If 50% inhibition of PDE activity is observed, an $IC_{50}$ value is calculated (concentration-response curves as described by Tallarida and Murray, *Manual of Pharmacologic Calculations with*

*Computer Programs*, Procedure 8, Graded Dose-response, pp. 14–19, Springer-Verlag, New York, 1981. The test provides an estimate of relative activity, potency and, through a measure of specificity, an estimate of the therapeutic index.

The compounds of formula I are also effective for treating urinary incontinence, including, for example, bladder detrusor muscle instability incontinence, stress incontinence, urge incontinence, overflow incontinence, enuresis, and post-prostectomy incontinence. Urinary incontinence can be caused by uncontrolled or unstable bladder contractions, particularly of the bladder detrusor muscle, which serves to force fluids out of the bladder. Bladder detrusor muscle instability may result in, for example, stress incontinence or urge incontinence, or combinations thereof, and/or enuresis. The major proportion of the neurohumeral stimulus for physiologic bladder contraction is acetylcholine-induced stimulation of postganglionic muscarinic receptor sites on bladder smooth muscle.

The present invention also relates to pharmaceutical compositions containing a therapeutically effective amount of one or more compounds of formula I, or a pharmaceutically acceptable salt thereof. A pharmaceutically acceptable carrier may also be included. Other therapeutic ingredients may also be included.

The term pharmaceutically acceptable salts refer to salts prepared from pharmaceutically acceptable non-toxic acids including inorganic acids and organic acids. Examples of acids that form pharmaceutically acceptable salts with compounds of Formula I include acetic acid, benzenesulfonic (besylate) acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid. The hydrochloric acid salt is particularly preferred.

Any suitable route of administration may be employed for providing the patient with an effective dosage of a compound of Formula I. For example, oral, rectal, parenteral (including subcutaneous, intramuscular, and intravenous) routes may be employed. Dosage forms include tablets, troches, dispersions, suspensions, solutions, capsules and patches. In particular, the composition may be formulated for oral administration, and may be in the form of a tablet or capsule.

Pharmaceutically acceptable carriers for use in the compositions of the present invention may take a wide variety of forms, depending on the forms preparation desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Oral syrups, as well as other oral liquid formulations, are well known to those skilled in the art, and general methods for preparing them are found in any standard pharmacy school textbook, for example *Remington: The Science and Practice of Pharmacy*. Chapter 86 of the 19th edition of Remington entitled "Solutions, Emulsions, Suspensions and Extracts" describes in complete detail the preparation of syrups (pages 1503–1505) and other oral liquids. Similarly, sustained or controlled release formulation is well known in the art, and Chapter 94 of the same reference, entitled "Sustained-Release Drug Delivery Systems," describes the more common types of oral and parenteral sustained-release dosage forms (pages 1660–1675.) The relevant disclosure, Chapters 84 and 96, is incorporated herein by reference. Because they reduce peak plasma concentrations, as compared to conventional oral dosage forms, controlled release dosage forms are particularly useful for providing a therapeutic plasma concentration of a compound of formula I while avoiding the side effects associated with high peak plasma concentrations that occur with conventional dosage forms.

The compositions may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 10 mg per day to about 1000 mg per day, preferably about 20 mg per day to about 500 mg per day, and more preferably, about 50 mg per day to about 250 mg per day, in single or divided doses. It is further recommended that children, patients over 65 years old, and those with impaired renal or hepatic function, initially receive low doses and that the dosage be titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Compounds of formula I having a cis-configuration may be synthesized from tramadol, which is commercially available as a racemic mixture of the (R,R)- and (S,S)-enantiomers. The enantiomers may be resolved using a modification of the procedure described in U.S. Pat. No. 3,652,589, as shown in Scheme 1, using D- or L-dibenzyl tartaric acid (DBTA) as appropriate.

Scheme 1
(Resolution of Cis-tramadol

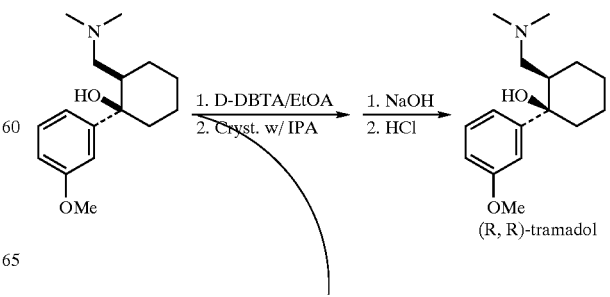

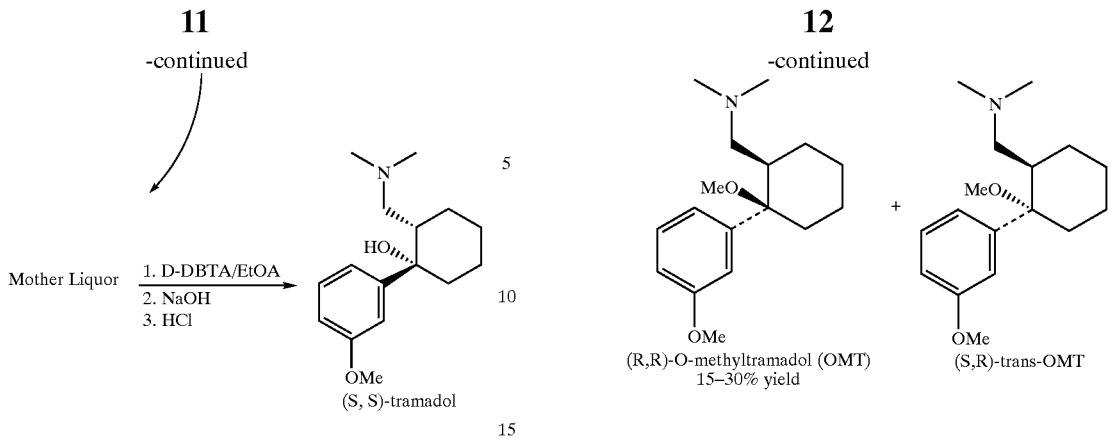

Other methods that may be used for the resolution of enantiomers include formation of diastereoisomeric salts or complexes or derivatives which may be separated, for example, by crystallization, gas-liquid or liquid chromatography; selective reaction of one enantiomer with an enantiomer-specific reagent, for example, enzymatic oxidation or reduction, followed by separation of the modified and unmodified enantiomers; and gas-liquid or liquid chromatography in a chiral environment, for example, on a chiral support, such as silica with a bound chiral ligand or in the presence of a chiral solvent. It will be appreciated that where the desired enantiomer is converted into another chemical entity by one of the separation procedures described above, a further step is typically required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Schemes 2 and 3 illustrate preparation of enantiomerically pure OMT and ODMOMT, starting from either enantiomerically pure cis-tramadol or from a racemic mixture of the (R,R)- and (S,S)-enantiomers. In Scheme 2, the hydroxy group at the 2-position of the cyclohexane ring of racemic tramadol, or one of its enantiomers, is methylated to yield a mixture of the cis- and trans-isomers of OMT. The cis-isomer may be isolated by crystallization. Scheme 3 shows procedure for this synthesis of ODMOMT by demethylation of OMT (from Scheme 2) using Ph₂PH and an alkyl lithium compound. Other cis-isomers of compounds of formula I may be synthesized from tramadol, using known procedures.

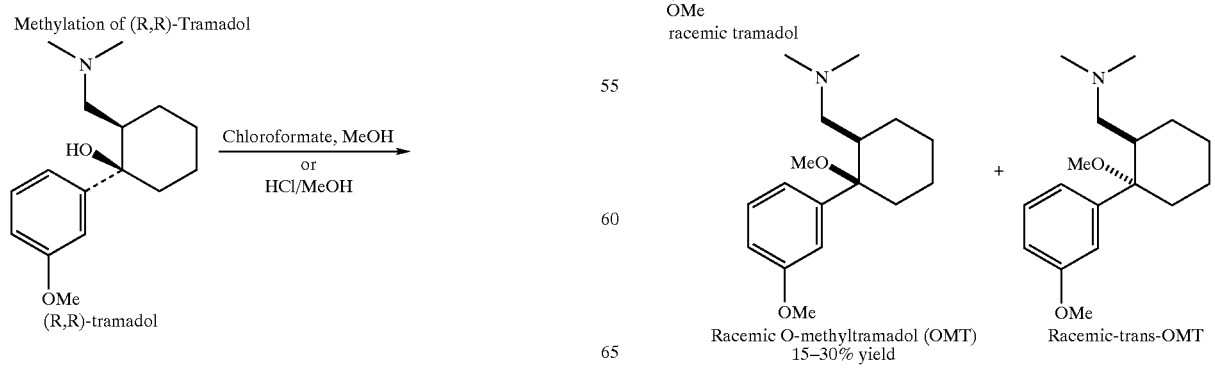

Scheme 3
(O-Demethylation of OMT)

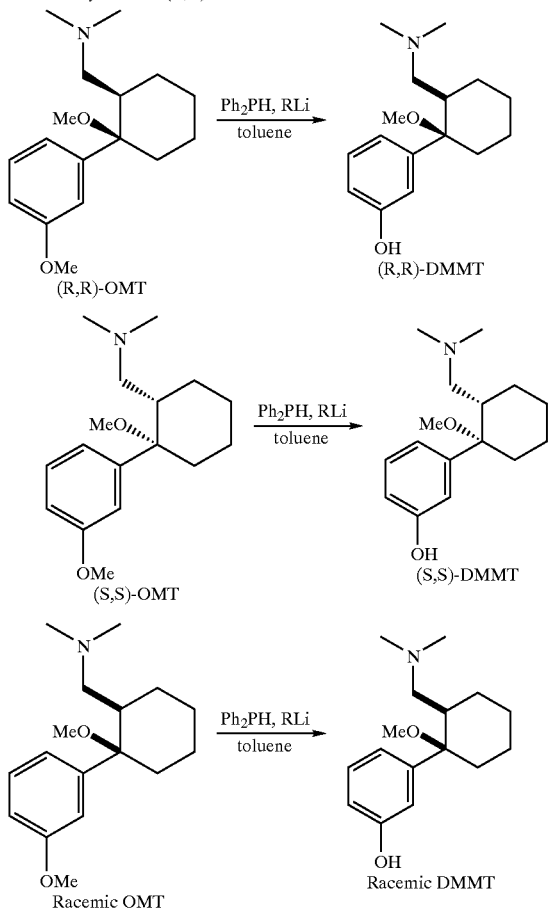

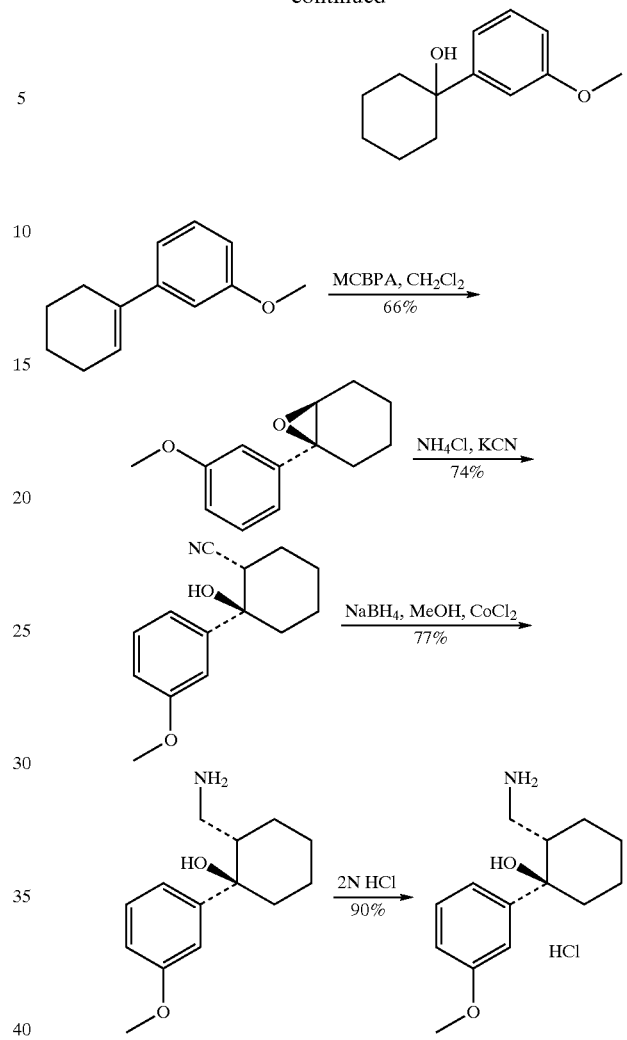

Procedures for the synthesis of compounds of formula I having a trans-configuration are illustrated in Schemes 4 through 8. An enantiomerically selective preparation of trans-tramadol is shown in Schemes 4–6. Scheme 7 shows demethylation of trans-tramadol using DIBAL. Preparation of racemic trans-OMT is shown in Scheme 8. Other trans-isomers of compounds of formula I may be synthesized from compounds shown in Schemes 4 or 6, for example, trans-N,N-demethyltramadol, or the nitrile analog shown in Scheme 4, using known procedures.

Scheme 4
(Racemic trans-N,N-Didesmethyltramadol)

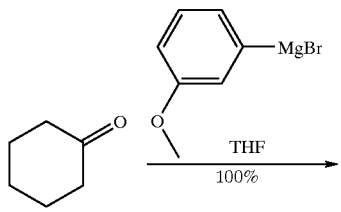

Scheme 5
(racemic trans-Tramadol)

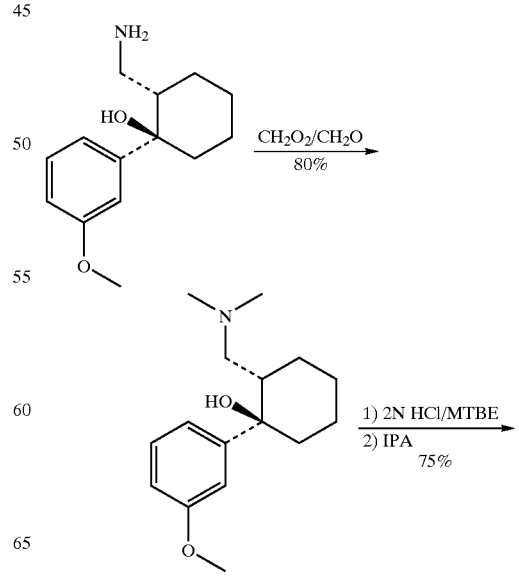

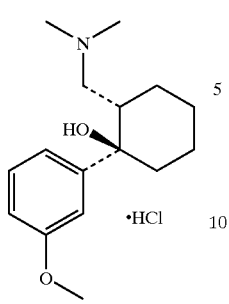
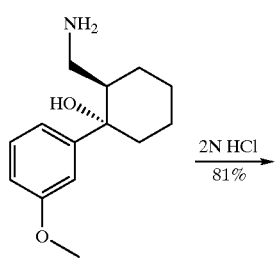
Scheme 6
Enantiomers of trans-Tramadol
(R,S)-trans-N, N-Desmethyltramadol
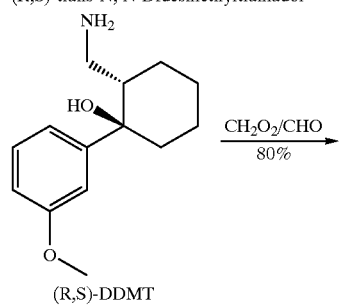
(S,R)-Trans-N,N-Didesmethyltramadol
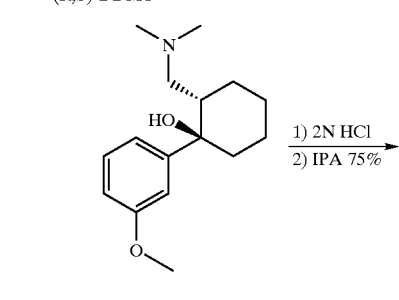
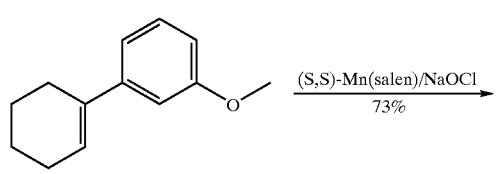
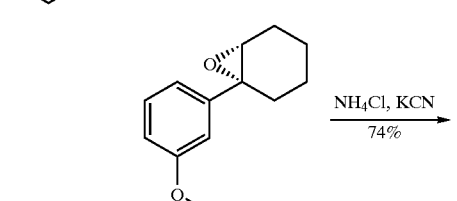
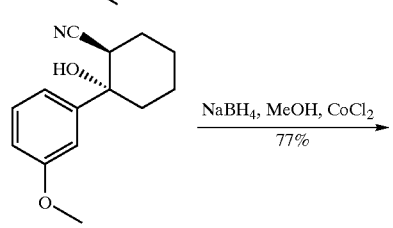
Scheme 7
Trans O-Desmethyltramadol
(demethylation with DIBAL to trans-ODMT)
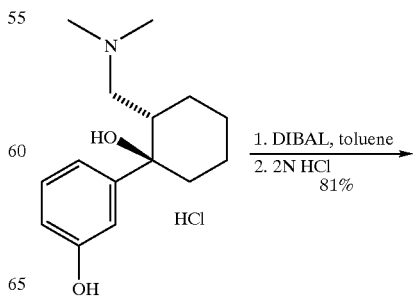

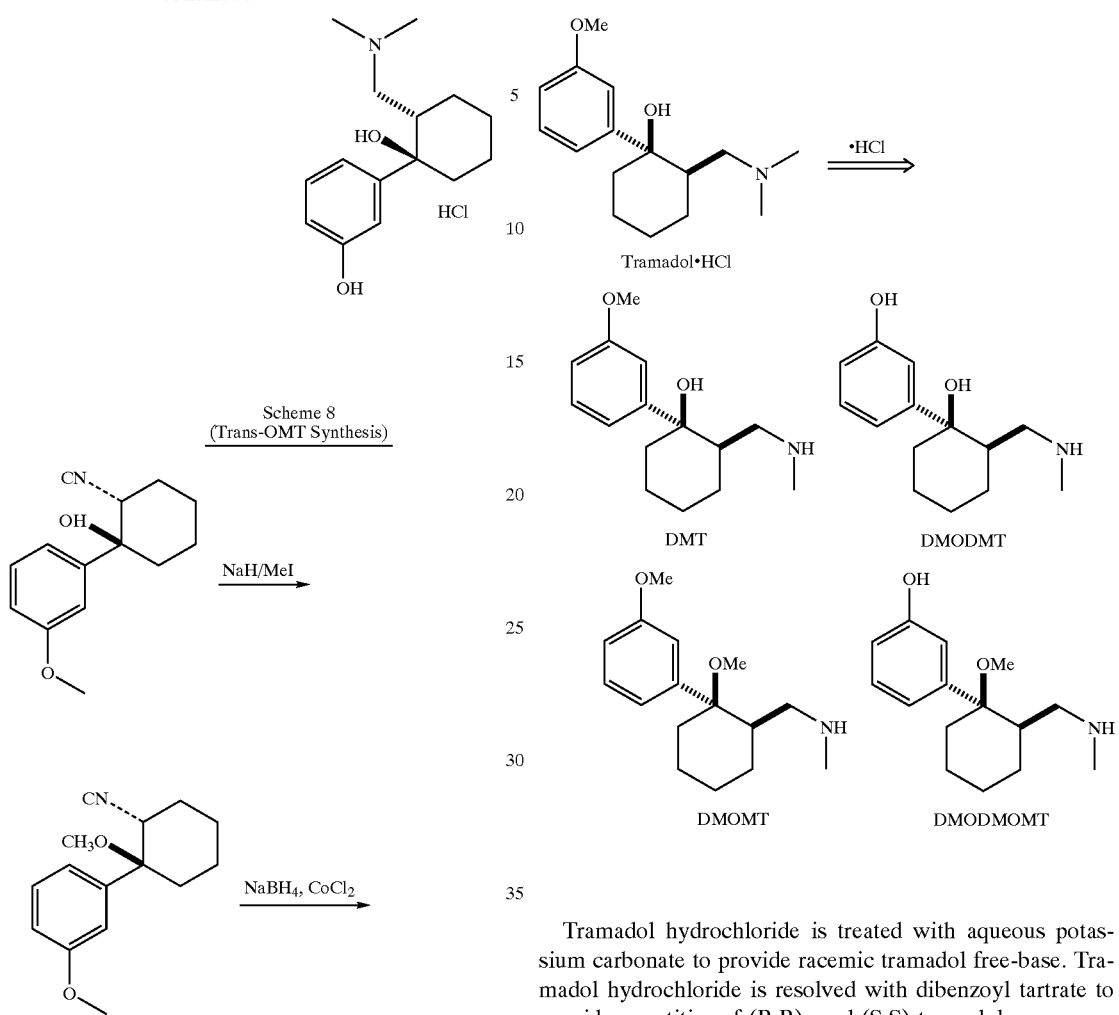

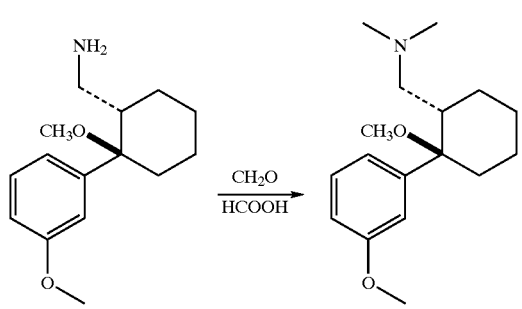

Tramadol hydrochloride is treated with aqueous potassium carbonate to provide racemic tramadol free-base. Tramadol hydrochloride is resolved with dibenzoyl tartrate to provide quantities of (R,R)- and (S,S)-tramadol.

Preparation of DMODMT is shown in Scheme 9. Tramadol free-base is N-demethylated with DEAD to provide DMT. The phenol functionality is then deprotected with DIBAL to provide DMODMT.

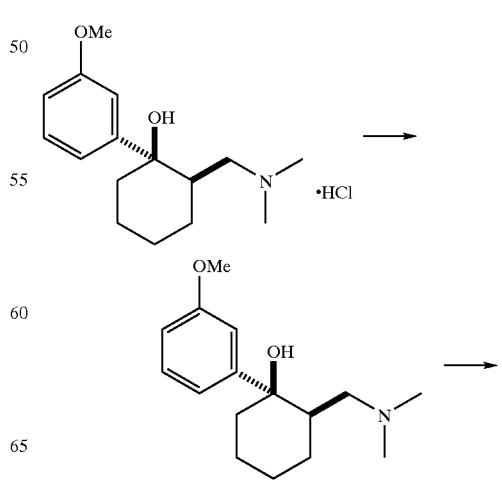

N-Desmethyl tramadol analogs may be prepared in quantities suitable for continued research and biological testing, starting with racemic tramadol hydrochloride. The synthsis is illustrated schematically below; products are designated: 1) desmethyltramadol (DMT) 2) desmethyl-O-desmethyltramadol (DMODMT) 3) desmethyl-O-methyltramadol (DMOMT) and 4) desmethyl-O-desmethyl-O-methyltramadol (DMODMOMT).

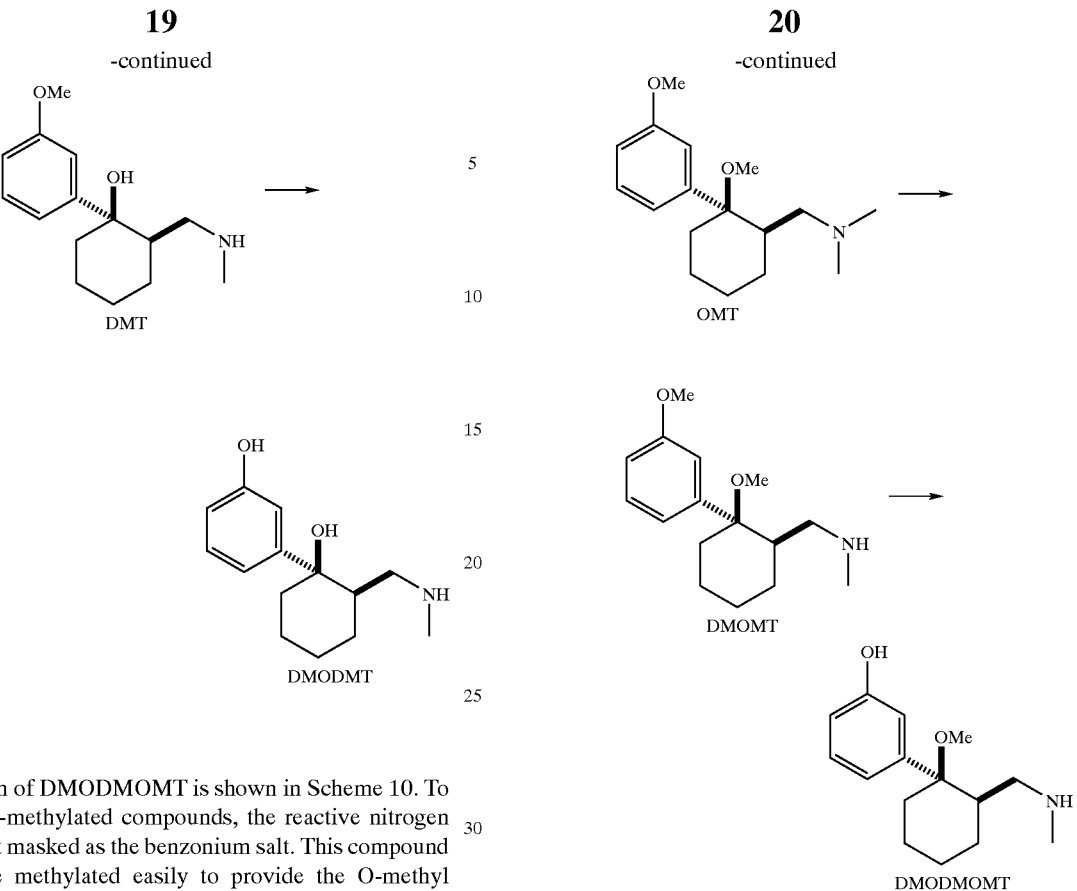

Preparation of DMODMOMT is shown in Scheme 10. To access the O-methylated compounds, the reactive nitrogen had to be first masked as the benzonium salt. This compound may then be methylated easily to provide the O-methyl framework. Removal of the N-benzyl group is effected with hydrogen gas over palladium to provide O-methyltramadol (OMT). OMT is demethylated with chloroethyl chloroformate to furnish DMOMT. The aryl-methyl ether is cleaved with LiPPh$_2$ and produced DMODMOMT.

A cyano analog of tramadol may be prepared according to the procedure illustrated in Scheme 11.

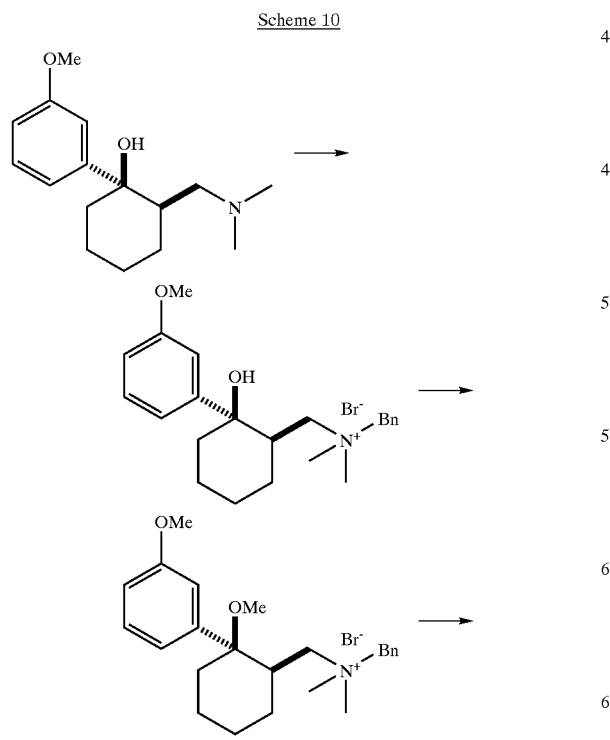

Scheme 10

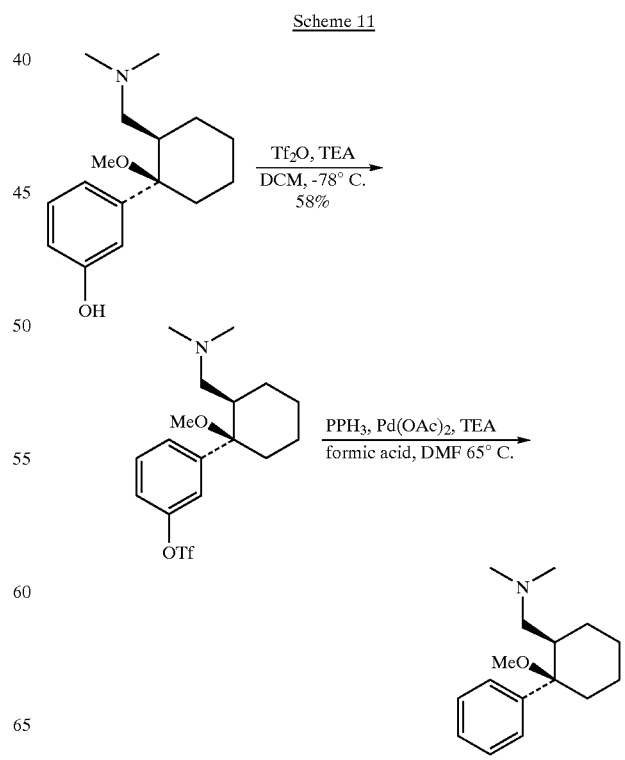

Scheme 11

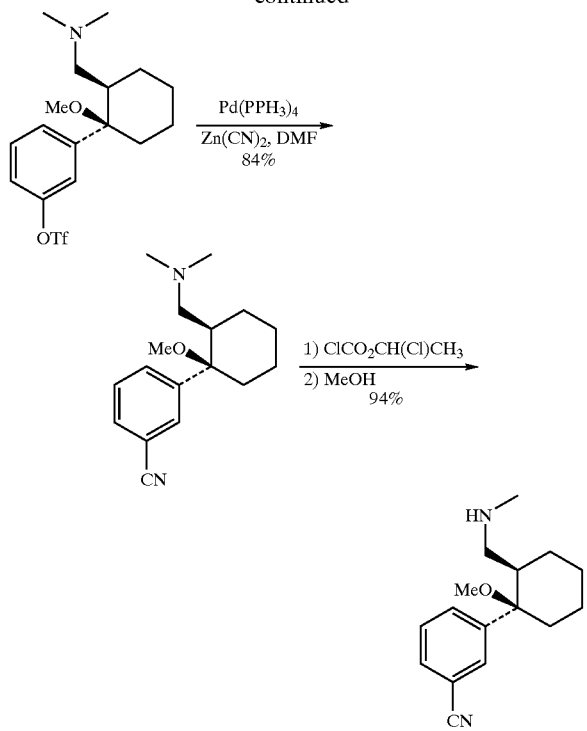

EXAMPLES

Synthesis of Tramadol Analogs and Diastereomers

General Procedure

Flash chromatography was performed on EM Science silica gel 60. Thin layer chromatography was performed using silica gel 60 $F_{254}$ plates, and compound visualization was effected with 10% $H_2SO_4$ containing 5% ammonium molybdate and 0.2% ceric sulfate. Chromatography was done with Merck silica gel 60 (70–230 mesh). All reactions were carried out in oven-dried glassware under an argon atmosphere. $^1$H NMR and $^{13}$C NMR were performed on a 300 MHz Varian instrument. J values are given in hertz.

Example 1.1

1-(m-Methoxyphenyl)cyclohexanol

To a 1L 3-neck RBF under argon was added magnesium (27.3 g, 1.12 mol) in THF (221 mL). 1,2-Dibromoethane (0.1 mL) was added. To the flask was added 3-bromide anisole (24.5 mL, 193 mmol) slowly over a 2 hour period. During the addition, the reaction mixture turned grayish and warmed to a gentle reflux. The addition was performed to maintain this gentle reflux. After the addition was complete, the reaction was allowed to cool to 22° C. and stirred for 2 h. Cyclohexanone (17.6 mL, 169.8 mmol) was slowly added to the reaction at 22° C. The reaction was stirred for 1 hour at room temperature, then a grayish precipitate formed. The reaction was cooled to 0° C., then 502 mL of 2N HCl was added slowly. The layers were separated. The organic layer was washed with water, dried ($MgSO_4$), filtered, and concentrated in vacuo to provide 39.4 g (99%) of 1-(m-Methoxyphenyl)cyclohexanol as an oil. $^1$H NMR ($CDCl_3$) δ1.81 (m, 10H), 3.85 (s, 3H), 6.82 (dd, J=8.1, 2.6 Hz, 1H), 7.12 (m, 2H), 7.29 (dd, J=10.6, 7.8 Hz, 1H). $^{13}$C-NMR δ* 22.4, 25.8, 39.1, 55.4, 73.4, 111.1, 112.0, 117.3, 129.4, 151.7, 159.8.

Example 1.2

1-Cyclohex-1-enyl-3-methoxy-benzene

A 1L 3-neck RBF under argon was charged with crude 1-(m-methoxyphenyl)cyclohexanol (59.2 g, 287 mmol). To the flask was added 592 mL of dry THF. The reaction was cooled to 0° C., and to it was slowly added $SOCl_2$ (58.6 mL, 803.6 mmol). After stirring for 10 minutes, pyridine (104 mL, 1.29 mol) was added slowly. The reaction mixture stirred slowly at 22° C. for 2 hours, and then it was cooled back to 0° C. 1N HCl (500 mL) was slowly added to the reaction. The layers were separated. The THF layer was dried ($MgSO_4$), filtered, and concentrated in vacuo. The crude product was chromatographed using 100% hexane as eluent to provide 39.5 g (82%, 2 steps) of product. $^1$H NMR ($CDCl_3$) δ1.72 (m, 2H), 1.83 (m, 2H), 2.24 (m, 2H), 2.45 (m, 2H), 3.86 (s, 3H), 6.18 (m, 1H), 6.83 (dd, J=8.1, 1.7 Hz, 1H), 6.98 (m, 1H), 7.03 (d, J=6.1 Hz, 1H), 7.27 (t, J=7.8 Hz, 1H).

Example 1.3

(+/−)-1-(3-Methoxy-phenyl)-7-oxa-bicyclo[4.1.0]heptane

A 1L 3-neck RBF under argon was charged with 1-Cyclohex-1-enyl-3-methoxy-benzene (8.0 g, 42.5 mmol). To the flask was added 520 mL of dry methylene chloride. The reactor was charged with meta-chloroperoxybenzoic acid (MCPBA) (16.87 g, 97.7 mmol) at room temperature. After stirring for 4 hours, a 10% aqueous solution of $Na_2S_2O_3$ (300 mL) was added to the reaction. The layers were separated. The organic layer was washed with 10% aqueous $NaHCO_3$. The layers were again separated, and the organic layer was dried ($MgSO_4$), filtered, and concentrated in vacuo. The crude product was chromatographed using 2% EtOAc/hexane as eluent to provide 6.35 g (73%) of epoxide. $^1$H NMR ($CDCl_3$) δ1.31–1.66 (m, 4H), 2.01 (m, 2H), 2.13 (m, 1H), 2.30 (m, 1H), 3.09 (t, J=2.2 Hz, 1H), 3.84 (s, 3H), 6.82 (m, 1H), 6.99 (m, 2H), 7.29 (m, 1H). $^{13}$C-NMR δ20.0, 20.3, 24.9, 29.2, 55.5, 60.5, 62.2, 110.9, 113.0, 118.1, 129.5, 144.5, 159.9. Mass spectrum (m/e) 204 ($M^+$).

Example 1.4

(S,S)-1-(3-Methoxy-phenyl)-7-oxa-bicyclo[4.1.0]heptane

A 500 mL 3-neck RBF under argon was charged with 1-Cyclohex-1-enyl-3-methoxy-benzene (16.9 g, 90.0 mmol). To the flask was added 112 mL of MTBE, 4-phenyl pyridine N-oxide (3.08 g, 18 mmol), and (R,R)—Mn(salen) (1.71 g, 2.7 mmol). The reaction was cooled to 0° C., and to it was added 193 g of bleach, buffered with $NaHCO_3$/NaOH to pH=11.5. After stirring overnight at 0° C., the layers were separated. The organic layer was washed with $H_2O$. The organic layer was dried ($MgSO_4$), filtered, and concentrated in vacuo. The crude product was chromatographed using 2% EtOAc/hexane as eluent to provide 13.4 g (73%) of (S,S)-epoxide. The ee was determined by HPLC (Chiralcel OD, mobile phase 95% hexane/5% IPA) by observing the (R,R) and (S,S)-isomers. (R,R)-isomer eluted at approximately 5.67 minutes. (S,S)-isomer eluted at approximately 6.91 minutes. The optical purity was 93.44% ee. $^1$H NMR ($CDCl_3$) δ1.31–1.66 (m, 4H), 2.01 (m, 2H), 2.13 (m, 1H), 2.30 (m, 1H), 3.09 (t, J=2.2 Hz, 1H), 3.84 (s, 3H), 6.82 (m, 1H), 6.99 (m, 2H), 7.29 (m, 1H). $^{13}$C-NMR δ20.0, 20.3, 24.9, 29.2, 55.5, 60.5, 62.2, 110.9, 113.0, 118.1, 129.5, 144.5, 159.9. Mass spectrum (m/e) 204 ($M^+$).

Example 1.5

(R,R)-1-(3-Methoxy-phenyl)-7-oxa-bicyclo[4.1.0]heptane

Prepared in a similar manner from 1-Cyclohex-1-enyl-3-methoxy-benzene as described for (S,S)-1-(3-Methoxy-phenyl)-7-oxa-bicyclo[4.1.0]heptane above using (S,S)—Mn(salen) as catalyst. The enantiomeric excess was 92.36%.

Example 1.6
(+/−)-2-Hydroxy-2-(3-methoxy-phenyl)-cyclohexanecarbonitrile

A 100 mL RBF under argon was charged with (+/−)-1-(3-Methoxy-phenyl)-7-oxa-bicyclo[4.1.0]heptane (4.76 g, 23.3 mmol). To the flask was added 42.3 mL of methanol, 5.23 mL of $H_2O$, 7.56 g (116.5 mmol) of KCN, and 2.73 g (51.26 mmol) of $NH_4Cl$. After stirring for 48 hours at reflux, the reaction was cooled to room temperature. EtOAc (300 ml) and $H_2O$ (300 ml) were added to the reaction. The dark layers were separated. The organic layer was washed with $H_2O$ (200 ml). The layers were separated, and the organic layer was dried ($MgSO_4$), filtered, and concentrated in vacuo. The crude product was chromatographed using 15% EtOAc/hexane to 20% EtOAc/hexane (gradient) as eluent to provide 4.0 g (74%) of nitrile. The (R,S)- and (S,R)-2-Hydroxy-2-(3-methoxy-phenyl)-cyclohexanecarbonitrile were prepared in a similar manner. $^1$H NMR ($CDCl_3$) δ1.79 (m, 7H), 2.22 (m, 1H), 2.45 (m, 1H), 3.03 (bs, 1H), 3.85 (s, 3H), 6.90 (m, 1H), 7.18 (m, 2H), 7.34 (m, 1H). $^{13}$C-NMR δ20.9, 21.5, 25.6, 33.4, 40.6, 55.5, 72.8, 111.8, 113.7, 117.9, 120.5, 129.9, 147.1, 160.0. Mass spectrum (m/e) 231 ($M^+$).

Example 1.7
(+/−)-trans-N,N-didesmethyltramadol HCl

A 500 mL RBF under argon was charged with (+/−)-2-hydroxy-2-(3-methoxy-phenyl)-cyclohexanecarbonitrile (3.12 g, 13.5 mmol). To the flask was added 78 mL of dry methanol, and $CoCl_2$ (3.51 g, 27.0 mmol) was added at room temperature. After stirring for 30 minutes at room temperature, the reaction mixture was cooled to 0° C., and $NaBH_4$ (5.13 g, 135.2 mmol) was added portion-wise to the blue reaction mixture over a 5 minute period. The reaction turned from a light blue color to black. The reaction mixture was warmed to room temperature, and stirred for 3 hours at room temperature. The reaction mixture was cooled to 0° C., then 3N HCl (109 mL) was slowly added. After stirring for an additional 30 minutes at 0° C., the volatiles were removed in vacuo. EtOAc (200 mL) was charged to the reaction mixture, and the layers were separated. The organic layer was discarded. The aqueous layer was treated with 2N NaOH until pH>12. The aqueous layer was extracted 3× with EtOAc (200 mL). The combined EtOAc layers were dried ($MgSO_4$), filtered, and concentrated in vacuo. The crude product was chromatographed using 2.4% $NH_4OH$/4.8% MeOH/92.8% EtOAc as eluent to provide 2.33 g (74%) of product. $^1$H NMR ($CDCl_3$) δ1.49–2.07 (m, 9H), 2.50 (dd, J=8.4, 12.8 Hz, 1H), 2.70 (dd, J=6.1, 12.8 Hz, 1H), 3.84 (s, 3H), 6.82 (ddd, J=1.0, 2.5, 7.9 Hz, 1H), 7.22 (m, 3H). $^{13}$C-NMR δ22.0, 23.2, 26.1, 37.7, 43.4, 49.4, 55.4, 75.5, 111.9, 113.0, 119.1, 128.9, 149.6, 159.6.

Example 1.8

The HCl salt was prepared as follows: A 100 mL RBF under argon was charged with (+/−)-2-aminomethyl-1-(3-methoxy-phenyl)-cyclohexanol (0.95 g, 4.0 mmol). To the flask was added 20 mL of dry MTBE. 2N HCl (4.0 mL, 8.0 mmol) was added dropwise at room temperature. After stirring for 1 hour at room temperature, the white precipitate was filtered in vacuo to provide 0.91 g (84%) of HCl salt. $^1$H NMR ($CD_3OD$) δ1.42–1.84 (m, 6H), 2.03 (m, 4H), 2.73 (m, 1H), 3.78 (s, 3H), 6.85 (d, J=8.3 Hz, 1H), 7.02 (m, 2H), 7.27 (t, J=7.7 Hz, 1H). $^{13}$C-NMR δ20.0, 21.7, 22.2, 27.5, 32.2, 38.0, 43.8, 55.7, 72.7, 112.6, 118.6, 129.5, 150.4, 159.8. Mass spectrum (m/e) 235 ($M^+$).

Example 1.9
(1S,2R)-(+)-trans-N,N-didesmethyltramadol HCl

Prepared in a similar manner from (1S,2R)-2-hydroxy-2-(3-methoxy-phenyl)-cyclohexanecarbonitrile as described for (+/−)-trans-N,N-didesmethyltramadol HCl above. The ee was determined by HPLC (Chiralcel OD, mobile phase 97.5% hexane/2.5% IPA/0.1% DEA) by observing the (R,S) and (S,R)-isomers. (S,R)-isomer eluted at approximately 5.68 minutes. (R,S)-isomer eluted at approximately 6.91 minutes. The optical purity was 92.2% ee. [α]=+23.4° (C. 0.10, EtOH).

Example 1.10
(1R,2S)-(−)-trans-N,N-didesmethyltramadol HCl

Prepared in a similar manner from (1R,2S)-2-hydroxy-2-(3-methoxy-phenyl)-cyclohexanecarbonitrile as described for (+/−)-trans-N,N-didesmethyltramadol HCl above. The optical purity was 93.4% ee. [α]=−22.9° (C. 0.14, EtOH).

Example 1.11
(+/−)-trans-Tramadol HCl

A 50 mL RBF was charged with (+/−)-trans-N,N-didesmethyltramadol (0.50 g, 2.12 mmol). To the flask was added formic acid (0.68 mL, 18.0 mmol), followed by a 37% aqueous solution of formaldehyde (1.20 mL) at room temperature. After stirring at reflux for 3 hours, the reaction was cooled to 0° C. A 25% aqueous solution of NaOH was slowly added to the reaction until the pH was greater than 11. The reaction was extracted 3× with EtOAc (50 mL). The combined EtOAc layers were dried ($MgSO_4$), filtered, and concentrated in vacuo. The crude product was chromatographed using 2% TEA/EtOAc as eluent to provide 0.34 g (61%) of product. $^1$H NMR ($CDCl_3$) δ1.51–2.20 (m, 9H), 2.12 (s, 6H), 2.29 (d, J=11.0 Hz, 1H), 2.42 (dd, J=4.2, 13.8 Hz, 1H), 3.84 (s, 3H), 6.80 (m, 1H), 7.25 (m, 3H).

Example 1.12

The HCl salt was prepared as follows. A 100 mL RBF under argon was charged with (+/−)-2-Dimethylaminomethyl-1-(3-methoxy-phenyl)-cyclohexanol (0.60 g, 2.28 mmol). To the flask was added 10 mL of dry MTBE. 2N HCl (2.28 mL, 4.56 mmol) was added dropwise at room temperature. After stirring for 1 hour at room temperature, the white precipitate was filtered in vacuo to provide 0.64 g (94%) of HCl salt. $^1$H NMR ($CD_3OD$) δ1.65–2.27 (m, 9H), 2.59 (dd, J=8.5, 13.1 Hz, 1H), 3.84 (s, 3H), 6.91 (dd, J=1.3, 9.1 Hz, 1H), 7.16 (m, 2H), 7.35 (dd, J=8.0, 8.2 Hz, 1H). $^{13}$C-NMR δ22.5, 22.7, 25.6, 36.1, 43.1, 43.4, 45.3, 55.9, 60.1, 74.9, 113.6, 113.7, 119.6, 130.7, 149.0, 161.5. Mass spectrum (m/e) 263.7 ($M^+$).

Example 1.13
(1S,2R)-(+)-trans-Tramadol HCl

Prepared in a similar manner from (1S,2R)-trans-N,N-didesmethyltramadol as described for (+/−)-trans-tramadol HCl above. The ee was determined by HPLC (Chiralcel OD, mobile phase 97.5% hexane/2.5% IPA/0.1% DEA) by observing the (R,S) and (S,R)-isomers. (S,R)-isomer eluted at approximately 5.75 minutes. (R,S)-isomer eluted at approximately 6.38 minutes. The optical purity was 95.39% er. [α]=+35.0° (C. 0.48, EtOH).

Example 1.14
(1R,2S)-(−)-trans-Tramadol HCl

Prepared in a similar manner from (1R,2S)-trans-N,N-didesmethyltramadol as described for (+/−)-trans-tramadol HCl above. The optical purity was 90.05% ee. [α]=−36.8° (C. 0.19, EtOH).

Example 1.15
(+/−)-trans-O-desmethyltramadol

A 100 mL 3-neck RBF under argon was charged with (+/−)-trans-tramadol (0.40 g, 1.52 mmol). To the flask was added toluene (1.56 mL). The reaction was cooled to 0° C., followed by the addition of DIBAL (6.58 mL, 6.58 mmol, 1M). After stirring at 0° C. for 30 minutes, the reaction was slowly warmed to 120° C. and allowed to reflux for 24 h. The reaction mixture was cooled to 0° C., and then quenched with 10 mL of EtOH. After stirring at 0° C. for 10 minutes, a 1:1:1 solution of EtOH/H$_2$O/toluene was added. The reaction mixture stirred an additional 10 minutes, upon which the solids were removed by filtration. The volatiles were removed in vacuo, then the reaction was extracted with EtOAc (100 mL) and H$_2$O (100 mL). The EtOAc layer was dried (MgSO$_4$), filtered, and concentrated in vacuo to provide 0.344 g of crude phenol (91%). $^1$H NMR (CD$_3$OD) δ1.64–2.26 (m, 8H), 2.60 (dd, J=4.7, 13.2 Hz, 1H), 2.72 (s, 6H), 3.20 (dd, J=8.5, 13.2 Hz, 1H), 3.34 (m, 1H), 6.75 (m, 1H), 7.05 (m, 2H), 7.24 (t, J=8.0 Hz, 1H). $^{13}$C-NMR δ22.5, 22.7, 25.7, 36.1, 43.4, 44.1, 60.1, 74.9, 114.5, 115.5, 118.4, 130.7, 148.9, 158.9. Mass spectrum (m/e) 249 (M$^+$).

The HCl salt was prepared as follows. A 100 mL RBF under argon was charged with (+/−)-trans-O-desmethyltramadol (1.0 g, 4.0 mmol). To the flask was added 10 mL of dry MTBE. 2N HCl (4.0 mL, 8.0 mmol) was added dropwise at room temperature. After stirring for 1 hour at room temperature, the white precipitate was filtered in vacuo to provide crude HCl salt. The crude HCl salt was dissolved in refluxing IPA (15 mL) and slowly allowed to cool to room temperature. After stirring for 1 hour at room temperature, the solids were collected by filtration to provide 0.78 g (68%) of (1R,2S)-trans-O-desmethyltramadol HCl as a white solid. $^1$H NMR (CD$_3$OD) δ1.64–2.26 (m, 8H), 2.60 (dd, J=4.7, 13.2 Hz, 1H), 2.72 (s, 6H), 3.20 (dd, J=8.5, 13.2 Hz, 1H), 3.34 (m, 1H), 6.75 (m, 1H), 7.05 (m, 2H), 7.24 (t, J=8.0 Hz, 1H). $^{13}$C-NMR δ22.5, 22.7, 25.7, 36.1, 43.4, 44.1, 60.2, 74.9, 114.5, 115.5, 118.4, 130.7, 148.9, 158.9. Mass spectrum (m/e) 249 (M$^+$).

Example 1.16
(1R,2S)-(−)-trans-O-desmethyltramadol HCl

Prepared in a similar manner from (1R,2S)-trans-tramadol as described for (+/−)-trans-O-desmethyltramadol HCl above. The ee, determined from the precursor (1R,2S)-trans-tramadol, by HPLC (Chiralcel OD, mobile phase 97.5% hexane/2.5% IPA/0.1% DEA) by observing the (R,S) and (S,R)-isomers. (S,R)-isomer eluted at approximately 5.78 minutes. (R,S)-isomer eluted at approximately 6.41 minutes. The optical purity was 95.05% er. [α]=−33.0° (C. 0.20, MeOH).

Example 1.17
(1S,2R)-(+)-trans-O-desmethyltramadol HCl

Prepared in a similar manner from (1S,2R)-trans-tramadol as described for (+/−)-trans-O-desmethyltramadol HCl above. The optical purity was 95.39% er. [α]=+31.2° (C. 0.22, MeOH).

Example 1.18
(+/−)-trans-2-Methoxy-2-(3-methoxy-phenyl)-cyclohexanecarbonitrile A 250 mL 3-neck RBF under argon was charged with (+/−)-2-Hydroxy-2-(3-methoxy-phenyl)-cyclohexanecarbonitrile (5.58 g, 22.77 mmol). To the flask was added tetrahydrofuran (100 mL). The reaction was cooled to −78° C., followed by the addition of NaH (0.655 g, 27.33 mmol, 60% dispersion in oil). After stirring at −78° C. for 10 minutes, MeI (7.08 mL, 113.8 mmol) was charged to the reaction. The reaction was slowly warmed to 0° C. and allowed to stir for 2 h. The reaction mixture was quenched with 0.1N HCl (10 mL) at 0° C., and then poured into a separatory funnel containing EtOAc (300 mL) and 0.1N HCl (300 mL). The layers were separated. The EtOAc layer was dried (MgSO$_4$), filtered, and concentrated in vacuo to provide crude methyl ether. The crude product was chromatographed using 5% EtOAc/hexane to 10% EtOAc/hexane as eluent to provide 5.47 g (92%) of pure methyl ether. $^1$H NMR (CDCl$_3$) δ1.59–1.88 (m, 6H), 2.20 (m, 3H), 2.98 (s, 3H), 3.05 (bs, 1H), 3.84 (s, 3H), 6.89 (ddd, J=1.0, 2.6, 8.3 Hz, 1H), 7.03 (m, 2H), 7.34 (t, J=7.8 Hz, 1H).

Example 1.19
(+/−)-trans-O-Methyldidesmethyltramadol

A 250 mL RBF under argon was charged with (+/−)-2-methoxy-2-(3-methoxy-phenyl)-cyclohexanecarbonitrile (2.70 g, 11.0 mmol). To the flask was added 64 mL of dry Methanol. CoCl$_2$ (2.87 g, 22.0 mmol) was added at room temperature. After stirring for 30 minutes at room temperature, the reaction mixture was cooled to 0° C., and NaBH$_4$ (4.19 g, 110 mmol) was added portion-wise to the blue reaction mixture over a 5 minute period. The reaction turned from a light blue color to black. The reaction mixture was warmed to room temperature, and stirred for 3 hours at room temperature. The reaction mixture was cooled to 0° C., then 3N HCl (90 mL) was slowly added. After stirring for an additional 30 minutes at 0° C., the volatiles were removed in vacuo. EtOAc (200 mL) was charged to the reaction mixture, and the layers were separated. The organic layer was discarded. The aqueous layer was treated with 2N NaOH until pH>12. The aqueous layer was extracted 3× with EtOAc (200 mL). The combined EtOAc layers were dried (MgSO$_4$), filtered, and concentrated in vacuo. The crude product was chromatographed using 2.4% NH$_4$OH/ 4.8% MeOH/92.8% EtOAc as eluent to provide 2.08 g (76%) of primary amine. $^1$H NMR (CDCl$_3$) δ1.53–1.88 (m, 7H), 2.06 (m, 2H), 2.16 (dd, J=4.3, 12.8 Hz, 1H), 2.55 (dd, J=9.3, 12.8 Hz, 1H), 2.92 (s, 3H), 3.83 (s, 3H), 6.81 (ddd, J=0.8, 2.4, 8.0 Hz, 1H), 6.95 (m, 2H), 7.28 (m, 1H).

Example 1.20
(+/−)-trans-O-Methyldidesmethyltramadol HCl

A 50 mL RBF under argon was charged with (+/−)-trans-O-Methyldidesmethyl tramadol (0.15 g, 0.6 mmol). To the flask was added 4 mL of dry MTBE. 1N HCl (1.2 mL, 1.2 mmol) was added dropwise at room temperature. After stirring for 1 hour at room temperature, the white precipitate was filtered in vacuo to provide HCl salt (0.14 g). The crude HCl salt was dissolved in refluxing IPA (15 mL) and slowly allowed to cool to room temperature. After stirring for 1 hour at room temperature, the solids were collected by filtration to provide 0.14 g (83%) of (+/−)-trans-O-Methyldidesmethyltramadol HCl as a white solid. $^1$H NMR (CD$_3$OD) δ1.49–2.20 (m, 10H), 2.87 (s, 3H), 3.26 (m, 1H), 3.77 (s 3H), 6.86 (dd, J=1.5, 7.0 Hz, 1H), 6.93 (m, 2H), 7.29 (t, 8.2 Hz, 1H). $^{13}$C-NMR δ20.4, 22.1, 23.0, 26.3, 39.4, 45.7, 55.8, 79.8, 113.7, 114.2, 120.2, 130.9, 145.9, 161.7. Mass spectrum (m/e) 218 (M$^+$—OMe).

Example 1.21
(+/−)-trans-O-Methyltramadol Fumaric Acid

A 50 mL RBF was charged with (+/−)-trans-O-Methyldidesmethyltramadol (0.90 g, 4.0 mmol). To the flask was added formic acid (1.28 mL, 33.9 mmol), followed by a 37% aqueous solution of formaldehyde (2.25 mL) at room temperature. After stirring at reflux for 3 hours, the reaction was cooled to 0° C. A 25% aqueous solution of NaOH was slowly added to the reaction until the pH was greater than 11. The reaction was extracted 3× with EtOAc (50 mL). The combined EtOAc layers were dried (MgSO$_4$), filtered, and concentrated in vacuo. The crude product was chromatographed using 2% TEA/EtOAc as eluent to provide 0.43 g (40%) of tertiary amine. $^1$H NMR (CDCl$_3$) δ1.39–2.06 (m, 10H), 1.97 (s, 6H), 2.37 (t, J=11.3 Hz, 1H), 2.89 (s, 3H), 3.80 (s, 3H), 6.80 (ddd, J=1.1, 2.4, 9.0 Hz, 1H), 6.92 (m, 2H), 7.27 (m, 1H). $^{13}$C-NMR δ19.9, 21.2, 23.2, 25.4, 27.1, 43.4, 45.8, 49.2, 49.6, 55.3, 57.9, 112.3, 112.7, 119.4, 129.0, 146.3, 159.8.

The fumaric acid salt was prepared as follows. (+/−)-trans-O-Methyltramadol (0.37 g, 1.35 mmol) was dissolved in 3 mL of methanol. To it at room temperature, was added a solution of fumaric acid (0.157 g, 1.35 mmol) in methanol (3 mL). The reaction mixture was stirred for 1 h. The solution was concentrated in vacuo to provide 0.53 g as a white foam (100%). $^1$H NMR (CD$_3$OD) δ1.55–1.87 (m, 6H), 2.11–2.31 (m, 4H), 2.59 (s, 6H), 2.93 (s, 3H), 3.33 (m, 1H), 3.83 (s, 3H), 5.51 (s, 3H), 6.93 (dd, J=2.5, 8.1 Hz, 1H), 7.02 (m, 2H), 7.37 (m, 1H). $^{13}$C-NMR δ20.6, 21.8, 24.4, 26.5, 42.8, 43.8, 54.9, 55.8, 58.2, 79.8, 114.1, 114.2, 120.4, 131.0, 136.4, 145.8, 161.7, 171.7. Mass spectrum (m/e) 392 (M$^+$−1).

Example 1.22
(+/−)-cis-Desmethylmethyltramadol

A 100 mL 3-neck RBF under argon was charged with diphenylphosphine (1.12 mL, 6.45 mmol). To the flask was added 12 mL of dry THF. The reaction was cooled to −10° C. A 1.6M solution of n-BuLi in hexanes (5.04 mL, 8.07 mmol) was slowly added dropwise to the reaction (internal temperature remained below 0° C.). After stirring for 30 minutes at 0° C., a THF solution of (+/−)-cis-Methyltramadol (0.40 g, 1.44 mmol, in 5 mL THF) was added dropwise at 0° C. The reaction stirred for 1 hour at 0° C., then warmed to reflux and stirred overnight. The next morning, the reaction was cooled to 0° C., and then was subsequently quenched with 3N HCl (20 mL). The layers were separated. The aqueous layer was washed with EtOAc (50 mL). The EtOAc layer was discarded. The aqueous layer was treated with solid K$_2$CO$_3$ until pH>12. The aqueous layer was washed 3× with EtOAc (50 mL). The combined EtOAc layers were dried (MgSO$_4$), filtered, and concentrated in vacuo. The crude product was chromatographed using 0.99% NH$_4$OH/4.9% MeOH/94% EtOAc as eluent to provide 0.18 g (48%) of phenol. $^1$H NMR (CDCl$_3$) δ1.26–2.13 (m, 10H), 1.98 (s, 6H), 2.36 (m, 1H), 3.25 (s, 3H), 6.64 (dd, J=2.3, 7.9 Hz, 1H), 6.78 (m, 1H), 6.82 (d, J=7.9 Hz, 1H), 7.18 (t, J=7.8 Hz, 1H). $^{13}$C-NMR δ22.1, 26.2, 28.0, 32.8, 45.4, 46.0, 50.4, 60.3, 80.8, 114.1, 114.4, 118.1, 129.3, 145.6, 157.1. Mass spectrum (m/e) 263 (M$^+$).

Example 1.23
(1R,2R)-(+)-Desmethylmethyltramadol

Prepared in a similar manner from (1R,2R)-cis-methyltramadol as described for (+/−)-cis-Desmethylmethyltramadol (DMMT) above. The ee, determined from the precursor (1R,2R)-cis-Tramadol, by HPLC (Chiralcel OD, mobile phase 97.5% hexane/2.5% IPA/0.01% DEA) by observing the (R,R) and (S,S)-isomers. (R,R)-isomer eluted at approximately 7.22 minutes. (S,S)-isomer eluted at approximately 11.04 minutes. The optical purity was >99.99% ee. [α]=+95.1° (C. 1.38, MeOH).

Example 1.24
(1S,2S)-(−)-Desmethylmethyltramadol

Prepared in a similar manner from (1S,2S)-cis-methyltramadol as described for (+/−)-cis-Desmethylmethyltramadol (DMMT) above. The optical purity was 99.83% er. [α]=−94.7° (C. 2.34, MeOH).

Example 1.25
(R,R)-tramadol-D-DBTA

Tramadol HCl (60 g) was suspended in EtOAc(400 mL), followed by addition of aqueous potassium carbonate (30 g) in water (60 mL). The reaction mixture was stirred for about 1 minute. The organic phase was separated, washed with water (30 mL), brine (30 mL), dried over Na2SO4 and filtered to remove Na$_2$SO$_4$. To the filtrate was added D-DBTA (73 g), in EtOAc (300 mL), and heated to reflux for 10 minutes. The solution was cooled to room temperature and stirred overnight. The solids (wet weight 84 g, 85% ee) were collected by filtration, (mother liquor was saved for the other enantiomer) and recrystallized in IPA (350 mL) to give 69 g diastereomerically pure salt (50 g, >99.9% ec). HPLC method. Chiral AD column, (hex:IPA:DEA=97.5:2.5:0.01). (R,R)-isomer 6.5 minutes, and (S,S)-isomer 9.9 minutes.

Example 1.26
(S,S)-Tramadol-L-DBTA

The mother liquors (670 ml) was treated with potassium carbonate (45 g) in water (200 mL). The organic phase was separated, washed with water, brine, dried over sodium sulfate, and filtered. The filtrate was treated with L-DBTA (36 g) in EtOAc (140 mL), heated to reflux and cooled to room temperature overnight. The solids were collected and dried to give (46 g,>99.5% ee) product. Enantiomers of tramadol free base were obtained by treatment of the DBTA salt with potassium carbonate.

Example 1.27
(S,S)-(−)-O-Desmethyltramadol HCl

To a solution of (S, S)-tramadol (4.5 g) in toluene (20 mL) at room temperature was added DIBAL (1M, 70 mL) in toluene. The reaction mixture was heated to 125–135° C. for 13 hours, cooled to 0–10° C., and EtOH (40 mL) was added slowly over 3 minutes. To the mixture were added additional EtOH (30 mL) and toluene (70 mL) and water (50 mL), and the mixture was stirred for 1 hour, to give a suspension. It was filtered and the solid was washed with EtOAc (30 mL). The filtrate was concentrated to a residue, dissolved in EtOAc (150 mL), and washed with water (70 mL), brine (50 mL), and dried over sodium sulfate (40 g). The dried solution was concentrated to give an oily product (4.2 g). It was dissolved in acetone and converted to its HCl salt by adding HCl/Ether to give a total of 4.8 g of the product. [α]$_D^{22}$=−35° (C. 1.1, MeOH). $^1$H NMR (DMSO-d$_6$) δ1.30–1.74 (m, 7H), 2.03 (m, 2H), 2.35–2.60 (m, 7H), 2.80 (m, 1H), 5.0 (s, 1H), 6.62 (m, 1H), 6.90 (m, 2H), 7.10 (m, 1H), 9.40 (s, 1H), 10.06(s, 1H). $^{13}$C-NMR δ21.1, 24.6, 26.1, 40.5, 44.8, 59.3, 73.7, 112.3, 113.3, 115.5, 128.9, 149.7, 157.2. The racemate and the (R,R)-(+)-isomer were prepared similarly with DIBAL. Optical rotation of the (+)-isomer: [α]$_D^{22}$=+35.0° (C. 1.0, MeOH).

Example 1.28
(R,R)-(+)-N-desmethyltramadol HCl (R,R)-tramadol (7.5 g) was dissolved in toluene (30 mL) and treated with DEAD (6.4 g). The reaction mixture was heated to 50–55° C. for 15 hours, and concentrated to a residue. It was dissolved in EtOH (40 mL) and saturated aqueous ammonium chloride (40 mL), and heated to reflux for 2 h. It was concentrated to remove EtOH, and to the residue was added EtOAc (200 mL), water (60 mL), and aqueous potassium carbonate (20 ml). The organic phase was separated and concentrated to give a crude product. The pure product was isolated by flash chromatography (EtOAc:MeOH:Et$_3$N=95:10:5) as an oil (ca 2.1 g). It was converted to its HCl salt in TBME (2.4 g). $[\alpha]_D^{22}$=+14.7° (C. 0.95, MeOH). ). $^1$H NMR (DMSO-d$_6$) δ1.24–1.92 (m, 7H), 2.16–2.35 (m 2H), 2.24(s, 3H), 3.78 (s, 3H), 5.15 (s, 1H), 6.80 (m, 1H), 7.05(s, 2H), 7.22 (m, 1H), 8.8 (s, 1H), 8.88 (s, 1H). $^{13}$C 21.1, 24.7, 25.1, 33.0, 41.5, 50.1, 54.9, 73.9, 111.0, 111.5, 117.2, 129.0, 149.9, 159.1. mass spec. M$^+$250. The racemate and the (S,S)-(–)-isomer were prepared similary with DEAD reagent and have the same $^1$H NMR and $^{13}$C-NMR.

Example 1.29
(R,R)-(+)-O-Methyltramadol (R,R)-tramadol (2.5 g) was dissolved in MeCN (20 mL) at room temperature, followed by addition of chloroethyl chloroformate (2.2 mL). The reaction mixture was stirred at room temperature for 14 hours, and followed by addition of MeOH (40 mL), heated at reflux for 3.5 h. The reaction mixture was cooled to room temperature, concentrated to remove solvents to give a residue, which was dissolved in EtOAc (40 mL), aqueous potassium carbonate (15 mL), and water (20 mL). The organic phase was separated and washed with water, brine and concentrated to give a white solid. It was collected by filtration and washed with hexane (10 mL) to give the crude product (1.26 g, 95% pure). It was re-crystallized with EtOAc/hexane (0.7 mL/12 mL) to give 860 mg pure product. $[\alpha]_D^{22}$=+46° (C. 1, MeOH). $^1$H NMR (CDCl$_3$) δ1.30–1.65 (m, 4H), 1.68–1.75 (m, 1H), 1.79–1.90 (m, 4H), 1.92 (s, 6H), 2.04–2.10 (m, 1H), 2.24–2.32 (m, 1H), 3.23 (s, 3H), 3.83(s, 3H), 6.75–6.80 (, 1H), 6.86–6.91 (m, 2H), 7.23–7.29 (m, 1H), $^{13}$C-NMR 21.9, 26.0, 27.0, 32.7, 45.7, 46.2, 50.2, 55.2, 60.0, 80.6, 111.0, 113.0, 119.1, 128.8, 145.8, 159.3. mass spec. M$^+$278. The racemate and the (S,S)-(–)-isomer were prepared similary with chloroethyl chloroformate. Stereochemistry (cis configuration) was further estabolished by single X-ray analysis.

Example 1.30
Tramadol free-base

Tramadol hydrochloride (145 g) was dissolved in 400 mL of a 10% aqueous K$_2$CO$_3$ solution with magnetic stirring. The clear solution was extracted three times with ethyl acetate, dried with anhydrous Na$_2$SO$_4$ and evaporated to dryness on a rotovap. The oily solid was diluted with toluene and evaporated again to produce a clear oil with some white solid (110 g). The oil was filter through silica (neat) to produce a clear oil (102 g). HPLC R$_t$=6.794 min.

Example 1.31
N-Desmethyltramadol (DMT)

Tramadol free-base (7.5 g) was dissolved in toluene (20 mL) and DEAD (6.4 g) was added. The solution was heated at 55° C. for 16 h. The mixture was evaporated and diluted with EtOH (40 mL) and saturated aqueous ammonium chloride (40 mL) and heated to reflux (110° C., bath) for 2 h. The mixture was again evaporated to an oily solid. The residue was dissolved in aqueous base (20 mL 10% K$_2$CO$_3$ and 60 mL H$_2$O) and extracted with ethyl acetate. The organic extracts were evaporated to yield a yellow solid (13.36 g). This residue was chromatographed {100 g flash Si, 2L 85:10:5 EA/MeOH/TEA, 50 mL/fract, #4–6} to yield a mixture of the expected product and reduced DEAD (7.29 g). Most of the impurity was removed by trituration with cold DCM. The extracted organic layers were evaporated to yield DMT as a yellow oil (3.55 g).

TLC R$_f$ (25% ammoniated methanol/DCM)=0.1. HPLC R$_t$=7.224 min. $^1$H NMR (CDCl$_3$, δ): 7.27 (t, 1H), 7.16 (S, 1H), 7.04 (m, 1H), 6.77 (dt, 1H), 3.84, (s, 3H), 2.58 (dd, 1H), 2.32 (dd, 1H), 2.23 (s, 3H), 2.0–1.2 (m, 9H). 13C NMR (CDCl3, δ): 159.4, 152.0, 128.8, 117.2, 111.1, 110.8, 87.0, 55.1, 53.4, 44.0, 40.5, 36.7, 26.4, 25.9, 21.9. HRMS calcd for C$_{15}$H$_{23}$NO$_2$: 249.1729, found (submitted).

Example 1.32
N-Desmethyl-O-Desmethyltramadol (DMODMT)

DMT (0.50 g) was dissolved in toluene (2 mL) and Dibal (2M in hexane, 10 mL) was added dropwise. Additional toluene (20 mL) was added and the hexane was distilled off (20 mL). The mixture was refluxed overnight and cooled. The mixture was chilled with ice-water and ethanol was added carefully (5 mL). Celite was added followed by 50% aqueous ethanol (10 mL). The slurry was stirred for 0.5 h and filtered, rinsing with ethyl acetate. The filtrate was evaporated to yield DMODMT as a cloudy oil (437.3 mg).

TLC R$_f$ (50% ammoniated methanol/DCM)=0.1. $^1$H NMR (CDCl$_3$, δ): 7.34 (m, 1H), 7.15 (t, 1H), 6.84 (m, 1H), 6.70 (d, 1H), 2.54 (d, 1H), 2.35 (d, 1H), 2.16 (s, 3H), 2.0–1.3 (m, 9H). HRMS calcd for C$_{14}$H$_{21}$NO$_2$: 235.1572, found (submitted).

Example 1.33
O-Methyltramadol (OMT)

Tramadol free-base (15.78 g) was dissolved in THF (100 mL) at ambient temperature. Benzyl bromide (8.8 mL, 1.24 eq) was added and the mixture was stirred for 1 h at ambient temperature and 23 h at 50° C. (bath). The mixture was cooled and diluted with hexanes (200 mL) to produce a white precipitate. The solid was collected by filtration, rinsing with ether. The solid was dried under vacuum (50° C., 5 h) to yield a free flowing white powder (27.03 g, 104%).

Part of the solid from above (15 g) was suspended in THF (180 mL). NaH (2.08 g, 1.5 eq) was added followed by MeI (3.24 mL, 1.5 eq). The mixture was heated at 55° C. (bath) for 22 h. The mixture was cooled to ambient temperature diluted with methanol until clear (~50 mL). The solution was then evaporated to a white powder (23.93 g).

The white powder from above was dissolved in aqueous methanol (120 mL MeOH, 20 mL H$_2$O) in a Parr bottle and Pd/C (1.0 g) was added. The bottle was placed in the shaker and pressurized to 50 PSIG. The pressure was released and reapplied three more time with intermittant shaking before the mixture was allowed to shake overnight (15 h) while the connection to the resevoir was open. The reaction was found to be 67% complete by HPLC analysis. An additional quantity of Pd/C (0.5 g) was added as a solution in methanol. The mixture was repressurized according to the above procedure and allowed to shake for 24 h. The mixture was filtered and evaporated. The yellow solid was dissolved in ethyl acetate and washed with 10% aqueous K$_2$CO$_3$. The organic layer was evaporated to yield an oily solid (9.5 g). The residue was chromatographed with a small amount of silica. Elution with an ethyl acetate/hexanes gradient yielded a clear oil (8.03 g). This oil could be crystallized from hot hexanes (20 mL) overnight to yield OMT (5.25 g) as white cubes.

HPLC R$_t$=8.148 min. $^1$H NMR (CDCl$_3$, δ): 7.25 (t, 1H), 6.9–6.8 (m, 2H), 6.76 (dd, 1H), 3.82 (s, 3H), 3.22 (s, 3H), 2.25 (m, 1H), 2.05 (m, 1H), 1.92 (s, 6H), 1.9–1.3 (m,9H). $^{13}$C NMR (CDCl3, δ): 159.3, 145.8, 128.8, 119.1, 113.0, 111.0, 80.6, 60.0, 55.2, 50.2, 46.2, 45.7, 32.7, 27.0, 26.0, 21.9. HRMS calcd for C$_{17}$H$_{27}$NO$_2$: 277.2042, found (submitted).

Example 1.34
N-Desmethyl-O-methyltramadol (DMOMT)

OMT (4.0 g, 14.41 mmol) was dissolved in DCE (40 mL) and to it was added 1-chloroethyl chloroformate (2.3 mL, 1.5 eq). The mixture was heated at 90° C. for 4 h before being evaporated to dryness. The residue was dissolved in anhydrous methanol (80 mL) and further heated at reflux (90° C., bath) for 2 h. Evaporation yielded the crude DMOMT as the hydrochloride salt. Chromatography was difficult due to tailing and acid-exchange but yielded 4.3 g of the amine in various forms. A portion was dissolved in DCM and precipitated with hexanes to yield white crystals of amine hydrochloride and a mother liquor containing amine free-base. Another sample was dissolved in ether, diluted with 4M HCl in dioxane (2 eq) and precipitated overnight in the freezer. A good recovery of white powder was obtained.

HPLC $R_t$=8.233. $^1$H NMR (CDCl$_3$, δ): 7.26 (t, 1H), 6.85 (d, 1H), 6.81 (s, 1H), 6.76 (dd, 1H), 3.78 (s, 3H), 3.22 (s, 3H), 2.6–2.9 (m, 2H), 2.44 (s, 3H), 2.4–1.3 (m, 9H). $^{13}$C NMR (CDCl3, δ): 159.8, 144.0, 129.7, 118.3, 112.4, 112.0, 80.8, 55.2, 50.7, 50.2, 44.8, 34.0, 31.8, 26.0, 25.0, 21.3. HRMS calcd for $C_{16}H_{25}NO_2$: 263.1885, found (submitted).

Example 1.35
N-Desmethyl-O-desmethyl-O-methyltramadol (DMODMOMT)

Diphenylphosphine (1.73 mL, 4.4 eq) was dissolved in THF (20 mL) and chilled to −10° C. (internal). NBuLi was added dropwise, keeping the temperature below 0° C., followed by stirring for 0.5 h. DMOMT (0.59 g, 2.240 mmol) was dissolved in THF (5 mL) and added dropwise to the mixture. Stirring for 0.5 h lead to a green solution. The solution was then refluxed (90° C. bath, 16 h), cooled, chilled to 0° C., and quenched with 3M aqueous HCl (30 mL). The aqueous layer was seperated and neutralized carefully with solid $K_2CO_3$ (~2 g) until saturated. The aqueous layer was extracted with ethyl acetate, dried with $Na_2SO_4$, and evaporated to yield a crude brown oil (1.43 g). The crude product was chromatographed (120 g ISCO column, 0→100% 0.1% ammoniated ethanol and DCM gradient) to yield DMODMOMT (458 mg, 82%) as a brown glass.

TLC $R_f$ (25% ammoniated methanol/DCM)=0.6. HPLC $R_t$=7.352 min. $^1$H NMR (CDCl$_3$, δ): 7.15 (t, 1H), 6.78 (d, 1H), 6.68 (s, 1H), 6.63 (d, 1H), 3.18 (s, 3H), 2.67 (m, 1H), 2.35 (m, 1H), 2.20 (s, 3H), 2.1–1.3 (m, 9H). $^{13}$C NMR (CDCl3, δ): 158.1, 144.8, 129.3, 116.5, 114.6, 113.6, 80.5, 52.1, 50.1, 46.8, 35.2, 31.7, 27.0, 25.5, 21.5. HRMS calcd for $C_{15}H_{23}NO_2$: 249.1729, found (submitted).

Example 1.36
Rac-O-Ethyltramadol

Tramadol N-benzyl salt (264 mg, 0.61 mmol) and NaH (60% dispersion in mineral oil, 37 mg, 0.92 mmol) were suspended in anhydrous DMF (6 mL) and cooled to 0° C. Iodoethane (74 μL, 0.92 mmol) was added and the suspension was allowed to stir and warm to room temperature. After 16 h, MeOH (3 mL) was added and the solution was concentrated in vacuo and used directly in the next reaction.

Crude ethyl tramadol N-benzyl salt (0.61 mmol) and 10% wt. Pd/C (150 mg) were suspended in 10:1 MeOH/H$_2$O (5.5 mL) in a 30 mL hydrogenation bomb. A stir bar was added, and the vessel was purged 3 times with H$_2$ then charged to 60 psi. After 16 hours the suspension was diluted with MeOH (3 mL) and filtered through celite. The celite was washed with MeOH and CH$_2$Cl$_2$ and the combined washes concentrated to an orange oil. Purification by silica gel column chromatography on an Isco combiflash system utilized a 35 g column and a gradient of 0→20% MeOH in CH$_2$Cl$_2$ over 20 min. To prepare the free base, the pure product was redissolved in EtOAc (50 mL), washed 3×20% aqueous NaOH, dried (Na$_2$SO$_4$), filtered and concentrated to yield rac-O-ethyltramadol (92 mg, 52%) as a white solid. HPLC $R_t$=8.79 min, $^1$H NMR (400 mHz, CDCl$_3$) 7.23 (at, 1H), 6.88–6.86 (m, 2H), 6.76–6.74 (m, 1H), 3.80 (s, 3H), 3.42–3.38 (m, 1H), 3.30–3.26 (m, 1H), 2.32 (dd, J=9.9, 12.1 Hz, 1H), 2.05–2.02 (m, 1H), 1.92 (s, 6H), 1.89–1.79 (3H), 1.69 (dd, J=2.2, 12.1 Hz, 1H), 1.63–1.34 (m, 5H), 1.24 (t, J=6.96 Hz, 3H); $^{13}$C NMR (100 mHz, CDCl$_3$) 159.9, 144. 129.9, 118.5, 112.7, 111.9, 79.4, 60.6, 57.1, 55.4, 44.2, 43.9, 32.5, 28.6, 24.9, 21.3, 15.3; mass spectrum (m/z) M$^+$291.

Example 1.37
Rac-O-Propyltramadol

Tramadol N-benzyl salt (284 mg, 0.65 mmol) and NaH (60% dispersion in mineral oil, 30 mg, 0.72 mmol) were suspended in anhydrous DMF (6 mL) and cooled to 0° C. Allyl bromide (74 μL, 0.85 mmol) was added and the suspension was allowed to stir and warm to room temperature. After 4 h, MeOH (3 mL) was added and the solution was concentrated in vacuo and used directly in the next reaction.

Crude allyl tramadol N-benzyl salt (0.65 mmol) and 10% wt. Pd/C (100 mg) were suspended in 10:1 MeOH/H$_2$O (7 mL) in a 30 mL hydrogenation bomb. A stir bar was added, and the vessel was purged 3 times with H$_2$ then charged to 30 psi. After 16 hours the suspension was diluted with MeOH (3 mL) and filtered through celite. The celite was washed with MeOH and CH$_2$Cl$_2$ and the combined washes concentrated to an orange oil. Purification by silica gel column chromatography on an Isco combiflash system utilized a 35 g column and a gradient of 0→20% MeOH in CH$_2$Cl$_2$ over 20 min. To prepare the free base, the pure product was redissolved in EtOAc (50 mL), washed 3×20% aqueous NaOH, dried (Na$_2$SO$_4$), filtered and concentrated to yield rac-O-propyltramadol (129 mg, 65%) as a white solid/oil. HPLC $R_t$=9.01 min, $^1$H NMR (400 mHz, CD$_3$OD) 7.10 (d, J=7.94 Hz, 1H), 6.75 (d, J=7.94 Hz, 1H), 6.70 (d, J=1.10 Hz, 1H), 6.63–6.60 (m, 1H), 3.58 (s, 3H), 3.12–3.00 (m, 2H), 2.77 (dd, J=9.1, 13.1 Hz, 1H), 2.52 (dd, J=1.59, 13.1 Hz, 1H), 2.28 (s, 6H), 1.85–1.31 (m, 11H), 0.78 (at, 3H); $^{13}$C NMR (100 mHz, CD$_3$OD) 161.5, 146.0, 130.9, 120.0, 113.8, 113.4, 80.6, 64.1, 61.4, 56.0, 45.2, 44.2, 33.4, 28.2, 25.9, 24.3, 22.7, 11.4; mass spectrum (m/z) (M$^+$+1) 306.

Example 1.38
Rac-O-Cyclopropylethyltramadol

Tramadol N-benzyl salt (244 mg, 0.56 mmol) and NaH (60% dispersion in mineral oil, 34 mg, 0.84 mmol) were suspended in anhydrous DMF (6 mL) and cooled to 0° C. Cyclopropylmethyl bromide (82 μL, 0.84 mmol) was added and the suspension was allowed to stir and warm to room temperature. After 16 h, NaH (60% dispersion in mineral oil, 34 mg, 0.84 mmol) and cyclopropylmethy bromide (82 μL, 0.84 mmol) were added and the mixture was heated to 70° C. for 16 h. The reaction was then cooled to room temperature and MeOH (3 mL) was added. The solution was concentrated in vacuo and used directly in the next reaction.

Crude cyclopropylmethyl tramadol N-benzyl salt (0.56 mmol) and 10% wt. Pd/C (100 mg) were suspended in 10:1 MeOH/H$_2$O (6 mL) in a 30 mL hydrogenation bomb. A stir bar was added, and the vessel was purged 3 times with H$_2$ then charged to 40 psi. After 17 hours the suspension was diluted with MeOH (3 mL) and filtered through celite. The celite was washed with MeOH and CH$_2$Cl$_2$ and the combined washes concentrated to an orange oil. Purification by silica gel column chromatography on an Isco combiflash system utilized a 35 g column and a gradient of 0→20% MeOH in $CH_2Cl_2$ over 20 min. To prepare the free base, the pure product was redissolved in EtOAc (50 mL), washed 3×20% aqueous NaOH, dried ($Na_2SO_4$), filtered and concentrated to yield rac-O-cyclopropylethyltramadol (132 mg, 75%) as a white solid/oil. HPLC $R_t$=9.28 min, $^1$H NMR (400 mHz, $CDCl_3$) 7.31 (at, 1H), 6.95–6.88 (m, 2H), 6.85–78 (m, 1H), 3.84 (s, 3H), 3.25 (dd, J=6.1, 9.3 Hz, 1H), 3.10 (at, 1H), 2.98 (dd, J=7.8, 13.1 Hz, 1H), 2.72 (d, J=13.1 Hz, 1H), 2.40 (s, 6H), 2.36–2.24 (at, 1H), 2.08–1.40 (m, 8H), 1.16–1.0 (in, 1H), 0.60–0.50 (m, 2H), 0.26–0.20 (m, 2H); $^{13}$C NMR (100 mHz, $CD_3OD$) 161.5, 145.8, 130.9, 120.0, 114.0, 113.4, 80.6, 67.2, 61.4, 56.0, 45.0, 44.2, 33.2, 28.2, 25.7, 22.8, 11.8, 3.60, 3.38; mass spectrum (m/z) ($M^+$+1) 318.

Example 1.39
Rac-O-Butyltramadol

Tramadol N-benzyl salt (256 mg, 0.59 mmol) and NaH (60% dispersion in mineral oil, 35 mg, 0.88 mmol) were suspended in anhydrous DMF (6 mL) and cooled to 0° C. 1-Bromobutane (95 µL, 0.88 mmol) was added and the suspension was allowed to stir and warm to room temperature. After 16 h, NaH (60% dispersion in mineral oil, 35 mg, 0.88 mmol) and 1-bromobutane (95 µL, 0.88 mmol were added and the mixture was heated to 70° C. for 16 h. The reaction was then cooled to room temperature and MeOH (3 mL) was added. The solution was concentrated in vacuo and used directly in the next reaction.

Crude butyl tramadol N-benzyl salt (0.59 mmol) and 10% wt. Pd/C (150 mg) were suspended in 10:1 MeOH/$H_2O$ (5.5 mL) in a 30 mL hydrogenation bomb. A stir bar was added, and the vessel was purged 3 times with $H_2$ then charged to 60 psi. After 17 hours the suspension was diluted with MeOH (3 mL) and filtered through celite. The celite was washed with MeOH and $CH_2Cl_2$ and the combined washes concentrated to an orange oil. Purification by silica gel column chromatography on an Isco combiflash system utilized a 35 g column and a gradient of 0→20% MeOH in $CH_2Cl_2$ over 20 min. To prepare the free base, the pure product was redissolved in EtOAc (50 mL), washed 3×20% aqueous NaOH, dried ($Na_2SO_4$), filtered and concentrated to yield rac-O-butyltramadol (54 mg, 75%) as a white solid/oil. HPLC $R_t$=9.75 min, $^1$H NMR (400 mHz, $CDCl_3$) 7.30 (at, 1H), 6.90–6.78 (m, 3H), 3.82 (s, 3H), 3.40–3.25 (m, 2H), 2.85 (dd, J=8.2, 13.1 Hz, 1H), 2.62 (d, J=12.9 Hz, 1H), 2.42–1.35 (m, 20H), 0.95 (at, 3H); $^{13}$C NMR (100 mHz, $CDCl_3$) 159.8, 145.2, 129.7, 118.6, 112.8, 111.7, 79.2, 61.1, 60.3, 55.3, 44.7, 43.9, 32.6, 32.1, 28.0, 25.3, 21.4, 19.6, 14.2; mass spectrum (m/z) $M^+$ Example 1.40
Rac-O-Desmethyl-O-Ethyltramadol A dry 2-neck flask equiped with a reflux condenser was charged with anhydrous THF (16 mL) and diphenyl phosphine (1.26 mL, 7.24 mmol). The clear solution was cooled to −10° C. and n-BuLi (2.5 M solution in hexane, 3.5 mL, 8.69 mmol) was added dropwise. The resultant bright orange solution was stirred for 30 min at −10° C., then O-ethyltramadol (470 mg, 1.61 mmol) in anhydrous THF (16 mL) was added dropwise. The orange solution was warmed to 0° C. and stirred for 1 h, then placed in an oil bath and heated to reflux for 16 h. After cooling to room temperature, the reaction was quenched with 2 N aqueous HCl (40 mL) and washed with EtOAc (3×30 mL). The organic washes were discarded. The aqueous phase was brought up to pH 12 with $K_2CO_3$, washed with EtOAc (3×30 mL), and the combined organic extracts were dried ($Na_2SO_4$), filtered and concentrated. Purification by silica gel column chromatography with 90/9/1 $CH_2Cl_2$/MeOH/ conc. $NH_4OH$ yielded rac-O-desnethyl-O-ethyltramadol (177 mg, 40%) as an off white solid. HPLC $R_t$=7.82 min, $^1$H NMR (400 mHz, $CDCl_3$) 8.20–7.9 (bs, 1H), 7.16 (at, 1H), 6.70 (d, J=7.7 Hz, 1H), 6.72 (s, 1H), 6.60 (dd,J=1.5,7.7 Hz, 1H), 3.41–3.28 (m, 2H), 2.36 (dd, J=9.2, 12.8 Hz, 1H), 2.14–2.02 (m, 2H), 1.96 (s, 6H), 1.90–1.30 (m, 8H), 1.23 (at, 3H); 3H); $^{13}$C NMR (100 mHz, $CDCl_3$) 157.0, 146.4, 129.0, 118.1, 114.4, 114.1, 80.2, 60.2, 56.8, 45.9, 45.3, 33.4, 28.0, 26.2, 22.1, 15.6; mass spectrum (m/z) $M^+$277.

Example 1.41
Rac-O-Desmethyl-O-Propyltramadol

A dry 2-neck flask equiped with a reflux condenser was charged with anhydrous THF (18 mL) and diphenyl phosphine (1.41 mL, 8.1 mmol). The clear solution was cooled to −10° C. and n-BuLi (2.5 M solution in hexane, 3.89 mL, 9.72 mmol) was added dropwise. The resultant bright orange solution was stirred for 30 min at −10° C., then O-propyltramadol (550 mg, 1.8 mmol) in anhydrous THF (16 mL) was added dropwise. The orange solution was warmed to 0° C. and stirred for 1 h, then placed in an oil bath and heated to reflux for 16 h. After cooling to room temperature the reaction was quenched with 2 N aqueous HCl (40 mL) and washed with EtOAc (3×30 mL). The organic washes were discarded. The aqueous phase was brought up to pH 12 with $K_2CO_3$, washed with EtOAc (3×30 mL), and the combined organic extracts were dried ($Na_2SO_4$), filtered and concentrated. Purification by silica gel column chromatography with 90/9/1 $CH_2Cl_2$/MeOH/ conc. $NH_4OH$ yielded rac-O-desmethyl-O-propyltramadol as an off white solid. An analytical sample was prepared by PTLC using a 1 cm plate and 20% MeOH/$CH_2Cl_2$. HPLC $R_t$=8.39 min, 1H NMR (400 mHz, $CDCl_3$) 7.14 (at, 1H), 6.81 (d, J=8.1 Hz, 1H), 6.72 (s, 1H), 6.60 (dd, J=1.8, 7.7 Hz, 1H), 3.27–3.22 (m, 2H), 2.32 (dd, J=8.8, 12.8 Hz, 1H), 2.12–2.02 (m, 2H), 1.95 (s, 6H), 1.88–1.48 (m, 9H), 1.49–1.25 (m, 2H), 0.98 (at, 3H); $^{13}$C NMR (100 mHz, $CDCl_3$) 156.9, 146.4, 129.0, 118.3, 114.4, 114.0, 79.8, 62.8, 60.3, 46.2, 45.5, 33.3, 28.1, 26.2, 23.6, 22.1, 11.1; mass spectrum (m/z) $M^+$291.

Example 1.42
Rac-O-Desmethyl-O-Cyclopropylethyltramadol

A dry 2-neck flask equiped with a reflux condenser was charged with anhydrous THF (6 mL) and diphenyl phosphine (469 µL, 8.1 mmol). The clear solution was cooled to −10° C. and n-BuLi (2.5 M solution in hexane, 1.3 mL, 3.24 mmol) was added dropwise. The resultant bright orange solution was stirred for 30 min at −10° C., then O-cyclopropylethyltramadol (190 mg, 0.6 mmol) in anhydrous THF (6 mL) was added dropwise. The orange solution was warmed to 0° C. and stirred for 1 h, then placed in an oil bath and heated to reflux for 16 h. After cooling to room temperature the reaction was quenched with 2 N aqueous HCl (40 mL) and washed with EtOAc (3×30 mL). The organic washes were discarded. The aqueous phase was brought up to pH 12 with $K_2CO_3$, washed with EtOAc (3×30 mL), and the combined organic extracts were dried ($Na_2SO_4$), filtered and concentrated. Purification by silica gel column chromatography with 90/9/1 $CH_2Cl_2$/MeOH/ conc. $NH_4OH$ yielded rac-O-desmethyl-O-cyclopropylethyltramadol as an off white solid. An analytical sample was prepared by PTLC using a 1 cm plate and 20% MeOH/$CH_2Cl_2$. HPLC $R_t$=8.42 min, $^1$H NMR (400 mHz, $CDCl_3$) 7.16 (at, 1H), 6.87 (d, J=8.1 Hz, 1H), 6.78 (d, J=1.8 Hz, 1H), 6.62 (dd, J=1.8, 7.33 Hz, 1H), 3.26–3.22 (m, 1H), 3.08–3.04 (m, 1H), 2.32 (dd, J=9.2, 12.5 Hz, 1H), 2.11–1.0 (m, 22H), 0.54–0.51 (m, 2H), 0.25–0.22 (m, 2H); mass spectrum (m/z) M⁺303.

Example 1.43

Rac-O-Desmethyl-O-Butyltramadol

A dry 2-neck flask equiped with a reflux condenser was charged with anhydrous THF (25 mL) and diphenyl phosphine (2.0 mL, 11.5 mmol). The clear solution was cooled to −10° C. and n-BuLi (2.5 M solution in hexane, 5.5 mL, 13.8 mmol) was added dropwise. The resultant bright orange solution was stirred for 30 min at −10° C., then O-butyltramadol (815 mg, 2.55 mmol) in anhydrous THF (15 mL) was added dropwise. The orange solution was warmed to 0° C. and stirred for 1 h, then placed in an oil bath and heated to reflux for 16 h. After cooling to room temperature the reaction was quenched with 2 N aqueous HCl (40 mL) and washed with EtOAc (3×30 mL). The combined organic extracts were dried ($Na_2SO_4$), filtered and concentrated. Purification by silica gel column chromatography with 90/9/1 $CH_2Cl_2$/MeOH/conc. $NH_4OH$ yielded rac-O-desnethyl-O-butyltramadol as an off white solid. An analytical sample was prepared by PTLC using a 1 cm plate and 20% MeOH/$CH_2Cl_2$. The clean material was dissolved in EtOAc (20 mL), washed with 20% aqueous NaOH, dried ($Na_2SO_4$), filtered and concentrated. HPLC $R_t$=8.76 min, ¹H NMR (400 mHz, $CDCl_3$) 7.8–7.4 (bs, 1H), 7.14 (at, 1H), 6.80 (d, J=7.70 Hz, 1H), 6.74 (d, J=1.0 Hz, 1H), 6.63–6.61 (m, 1H), 3.30–3.28 (m, 2H), 2.35 (dd, J=8.43, 12.5 Hz, 1H), 2.17–2.02 (m, 2H), 1.98 (s, 6H), 1.87–1.32 (m, 13H), 0.95 (at, 3H); ¹³C NMR (100 mHz, $CDCl_3$) 157.0, 146.3, 129.0, 118.2, 114.4, 114.0, 79.8, 61.0, 60.3, 46.0, 45.2, 33.2, 32.5, 28.2, 26.2, 22.1, 19.8, 14.4; mass spectrum (m/z) (M⁺+1) 320.

Example 1.44

2,3,4,6-Tetra-O-Benzyl-α-D-Glucopyranoside Trichloroacetimidate 2,3,4,6-tetra-O-benzyl-α-D-glucopyranoside (2.03 g, 3.75 mmol) was dissolved in $CH_2Cl_2$ (37 mL) and cooled to −20° C. DBU (56 mL, 0.38 mmol) was added, followed by trichloroacetonitrile (3.76 mL, 37.5 mmol). The resulting slightly orange solution was stirred and warmed to room temperature over 2 h, then filtered through a pad of silica gel. The silica gel was washed with 40% EtOAc/hexanes (200 mL) and the washes concentrated to give 2.57 g (quant.) of 2,3,4,6-tetra-O-Benzyl-α-D-glucopyranoside trichloroacetimidate as an orange oil. ¹H NMR (400 mHz, $CDCl_3$) 8.57 (s, 1H), 7.31–7.13 (m, 23H), 6.52 (d, J=3.3 Hz, 1H), 4.96 (d, J=11.0 Hz, 1H), 4.83 (at, 2H), 4.74 (d, J=11.7 Hz, 1H), 4.68 (d, J=11.7 Hz, 1H), 4.60 (d, J=12.1 Hz, 1H), 4.52 (d, J=10.6 Hz, 1H), 4.48 (d, J=12.1 Hz, 1H), 4.07–3.97 (m, 2H), 3.81–3.74 (m, 4H), 3.66 (dd, J=1.83, 11.0 Hz, 1H).

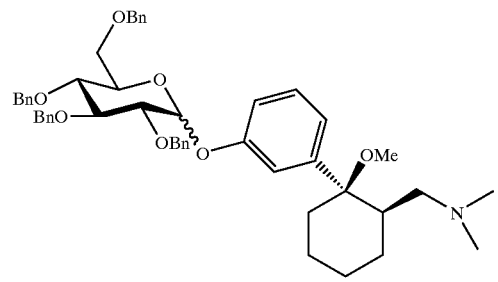

Diastereomer A

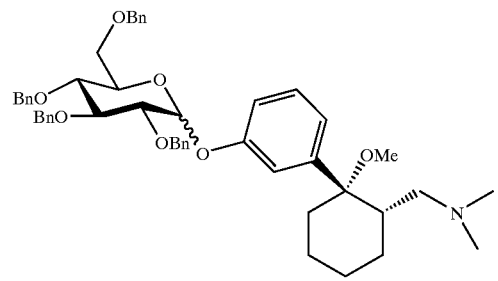

Diastereomer B

Example 1.45

Tramadol methyl ether phenol (27 mg, 0.10 mmol) and 2,3,4,6-tetra-O-Benzyl-α-D-glucopyranoside trichloroacetimidate (103 mg, 0.15 mmol) were azeotroped with toluene (3×2 mL) then dried under high vacuum for 16 h. The mixture was dissolved in $CH_2Cl_2$ (2 mL) and cooled to 0° C. TMSOTf (40 mL, 0.22 mmol) was added and the resulting orange solution was allowed to warm to room temperature over 1 h. The reaction was concentrated and purified by PTLC using a 1 cm plate and 10% MeOH/$CH_2Cl_2$ to give 35 mg (45%) of a mixture of 4 diastereomers as a clear oil. Achiral HPLC $R_t$=12.0, 12.2 min. Purification by chiral HPLC provided pure α-diastereomers and a mixture of β diastereomers. Chiral HPLC AD column, 1 ml/min, 254 nm, 95:5 hexanes:isopropanol. α-diastereomer A. $R_t$=5.54 min: ¹H NMR (400 mHz, $CDCl_3$) 7.40–7.22 (m, 19H), 7.15–7.13 (m, 2H), 7.04 (s, 1H), 6.97–6.95 (m, 2H), 5.45 (d, J=3.67 Hz, 1H), 5.07 (d, J=11.0 Hz, 1H), 4.91–4.80 (m, 3H), 4.68 (d, J=12.1 Hz, 1H), 4.58 (d, J=12.1 Hz, 1H), 4.50 (d, J=10.6 Hz, 1H), 4.42 (d, J=12.1 Hz, 1H), 4.21 (at, 1H), 3.92–3.88 (m, 1H), 3.83 (at, 1H), 3.74 (dd, J=3.30, 9.53 Hz, 2H), 3.57–3.55 (m, 1H), 3.19 (s, 3H), 3.26 (dd, J=9.5, 11.7 Hz, 1H), 2.16 (s, 1H), 2.06–2.02 (m, 2H), 1.89–1.80 (m, 10H), 1.70–1.37 (m, 7H); ¹³C NMR (100 mHz, $CDCl_3$) 156.9, 146.2, 139.0, 138.3, 138.2, 137.9, 129.0, 128.7, 128.6, 128.6, 128.6, 128.3, 128.1, 128.1, 127.9, 127.8, 121.0, 116.0, 114.8, 96.0, 82.3, 80.7, 80.0, 76.0, 75.4, 73.7, 73.6, 71.0, 68.3, 60.2, 50.4, 46.4, 45.9, 32.8, 27.2, 26.2, 22.1; mass spectrum (m/z) M⁺786. α diastereomer B: $R_t$=9.19 min: ¹H NMR (400 mHz, $CDCl_3$) 7.40–7.21 (m, 20H), 7.14–7.12 (m, 2H), 7.01–6.97 (m, 3H), 5.48 (d, J=3.30 Hz, 1H), 5.06 (d, J=10.6 Hz, 1H), 4.91–4.80 (m, 4H), 4.68 (d, J=11.7 Hz, 1H), 4.57 (d, J=12.1 Hz, 1H), 4.59 (d, J=10.6Hz, 1H), 4.41 (d, J=11.7 Hz, 1H), 4.21 (at, 1H), 3.89 (d, J=9.9 Hz, 1H), 3.83–3.71 (m, 3H), 3.54–5.51 (m, 1H), 3.19 (s, 3H), 2.28 (dd, J=9.9, 11.7 Hz, 1H), 2.16–2.02 (m, 2H), 1.91–1.81 (m, 9H), 1.71–1.25 (m, 8H); ¹³C NMR (100 mHz, $CDCl_3$) 156.9, 146.1, 139.0, 138.3, 128.9, 128.7, 128.6, 128.6, 128.6, 128.2, 128.2, 128.1, 128.0, 127.9, 121.1, 115.8, 114.9, 95.9, 82.3, 80.7, 79.9, 77.6, 76.0, 75.4, 73.7, 73.5, 71.0, 68.3, 60.2, 50.4, 46.3, 45.9, 32.8, 27.3, 26.2, 22.1. mass spectrum (m/z) M+786.

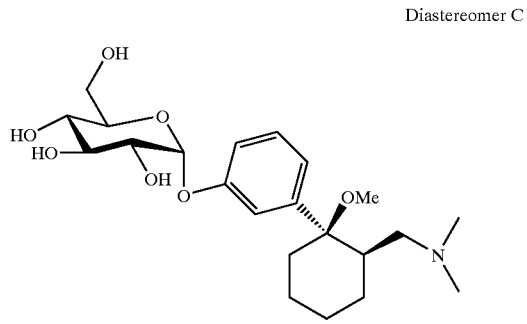

Diastereomer C

Example 1.46
Diastereomer A

Diastereomer A (36 mg, 0.046 mmol) and 10% wt. Pd/C (50 mg) were suspended in 10:1 MeOH:H$_2$O (3.3 mL) in a 30 mL hydrogenation bomb. A stir bar was added, and the vessel was purged 3 times with H$_2$ then charged to 50 psi. After 17 hours the suspension was diluted with MeOH (3 mL) and filtered through celite. The celite was washed with MeOH and the combined washes concentrated to give 15 mg (79%) of product as an orange/whitish solid. HPLC R$_t$=6.35 min; $^{13}$C NMR (100 mHz, CD$_3$OD) 159.1, 145.6, 131.3, 122.2, 117.5, 117.2, 99.9, 81.6, 75.2, 73.5, 72.1, 63.0, 61.8, 51.1, 46.7, 45.2, 43.7, 32.7, 28.5, 26.0, 23.0; mass spectrum (m/z) M+

Synthesis of 3-Cyano-tramadol (3-(2-Dimethylaminomethyl-1-methoxy-cyclohexyl)-benzonitrile):

General Procedure:

Flash chromatography was performed on EM Science silica gel 60. Thin layer chromatography was performed using silica gel 60 F$_{254}$ plates, and compound visualization was effected with 10% H$_2$SO$_4$ containing 5% ammonium molybdate and 0.2% ceric sulfate. All reactions were carried out in oven-dried glassware under an argon atmosphere. $^1$H NMR and $^{13}$C NMR were performed on a 300 MHz Varian instrument. TMS and CDCl$_3$ were used as internal standards for $^1$H and $^{13}$C spectra, respectively. J values are given in hertz.

Example 1.47
(+/−)-Trifluoro-methanesulfonic Acid 3-(2-dimethylaminomethyl-1-methoxy-cyclohexyl)-phenyl Ester To a magnetically stirred solution of (+/−)-cis-desmethylmethyltramadol (0.48 g, 1.82 mmol) in anhydrous methylene chloride (24 mL) at room temperature under Ar atmosphere was added TEA (0.86 mL, 7.28 mmol). The reaction mixture was cooled to −78° C. Trifluoromethane sulfonic anhydride (0.42 mL, 2.54 mmol) was added, and the mixture was warmed to room temperature. After 1 h, water (50 mL) was added, and the aqueous phase was extracted with dichloromethane (2×60 mL). The combined organic layers were washed with water, dried (MgSO$_4$), and concentrated in vacuo to the crude product. The pure product was obtained by column chromatography over silica gel (0.25:100 TEA/EtOAc as eluent) which gave the title compound (0.42 g, 58%). $^1$H NMR (CDCl$_3$) δ1.36–1.62 (m, 8H), 1.77 (m, 1H), 1.85 (s, 6H), 2.05 (dd, J=1.1, 14.3 Hz, 1H), 2.23 (dd, J=9.5, 12.1 Hz, 1H), 3.18 (s, 3H), 7.11 (dd, J=2.2, 8.0 Hz, 1H), 7.20 (t, J=2.2 Hz, 1H), 7.29 (d, J=8.0 Hz, 1H), 7.39 (t, J=8.0 Hz, 1H). $^{13}$C NMR (75 MHz, CDCl$_3$) 21.9, 26.0, 27.2, 32.7, 45.7, 46.6, 50.3, 60.0, 80.6, 119.3, 120.1, 126.6, 130.0, 147.9, 149.8.

Example 1.48
(+/−)-(2-Methoxy-2-phenyl-cyclohexylmethyl)-dimethyl-amine HCl

To a magnetically stirred solution of (+/−)-trifluoromethanesulfonic acid 3-(2-dimethylaminomethyl-1-methoxy-cyclohexyl)-phenyl ester (0.48 g, 1.21 mmol) in anhydrous DMF (2.42 mL) at room temperature under Ar atmosphere were added successively TEA (0.449 mL, 3.63 mmol), triphenylphosphine (12.6 mg, 0.048 mmol), Pd(OAc)$_2$ (5.4 mg, 0.0242 mmol), and formic acid (0.091 mL, 2.42 mmol). After stirring at 65° C. for 3 hours, the reaction was cooled to room temperature. Water (60 mL) was added, and the aqueous phase was extracted with EtOAc (2×100 mL). The combined organic layers were washed with water, dried (MgSO$_4$), and concentrated in vacuo to the crude product. The pure amine was obtained by column chromatography over silica gel (0.5:100 TEA/EtOAc as eluent) which gave the free base (0.251 g, 84%).

The HCl salt was prepared as follows. To a 50 mL RBF under argon was charged with (+/−)-(2-Methoxy-2-phenyl-cyclohexylmethyl)-dimethyl-amine (0.251 g, 1.01 mmol). To the flask was added 5 mL of dry MTBE. 2N HCl (0.80 mL, 1.60 mmol) was added dropwise at room temperature. After stirring for 1 hour at room temperature, the white precipitate was filtered in vacuo to provide 0.22 g (77%) of HCl salt. $^1$H NMR (CDCl$_3$) 1.45–1.97 (m, 7H), 2.10 (s, 3H), 2.14 (m, 1H), 2.38 (d, J=11.3 Hz, 1H), 2.54 (s, 3H), 2.73 (d, J=12.4 Hz, 1H), 2.86 (dd, J=7.7, 12.8 Hz, 1H), 3.22 (s, 3H), 7.28 (m, 3H), 7.39 (m, 2H). $^{13}$C NMR (75 MHz, CDCl$_3$) 22.8, 25.6, 28.2, 32.5, 42.4, 44.8, 45.7, 50.7, 61.3, 81.4, 127.9, 128.6, 129.9, 143.5. Mass spectrum (m/e) 249.0 (M+).

Example 1.49
(1R,2R)-(2-Methoxy-2-phenyl-cyclohexylmethyl)-dimethyl-amine HCl To a magnetically stirred solution of (1R,2R)-trifluoromethanesulfonic acid 3-(2-dimethylaminomethyl-1-methoxy-cyclohexyl)-phenyl ester (0.43 g, 1.09 mmol) in anhydrous DMF (2.15 mL) at room temperature under Ar atmosphere were added successively TEA (0.40 mL, 3.23 mmol), triphenylphosphine (12.6 mg, 0.042 mmol), Pd(OAc)$_2$ (4.8 mg, 0.021 mmol), and formic acid (0.082 mL, 2.18 mmol). After stirring at 65° C. for 3 hours, the reaction was cooled to room temperature. Water (60 mL) was added, and the aqueous phase was extracted with EtOAc (2×100 mL). The combined organic layers were washed with water, dried (MgSO$_4$), and concentrated in vacuo to the crude product. The pure amine was obtained by column chromatography over silica gel (0.5:100 TEA/EtOAc as eluent) which gave the free base (0.27 g, 100%).

The HCl salt was prepared as follows. To a 50 mL RBF under argon was charged with (1R,2R)-(2-methoxy-2-phenyl-cyclohexylmethyl)-dimethyl-amine (0.27 g, 1.09 mmol). To the flask was added 5 mL of dry MTBE. 2N HCl (0.80 mL, 1.60 mmol) was added dropwise at room temperature. After stirring for 1 hour at room temperature, the white precipitate was filtered in vacuo to provide 0.20 g (64%) of HCl salt. $^1$H NMR (CDCl$_3$) 1.45–1.97 (m, 7H), 2.10 (s, 3H), 2.14 (m, 1H), 2.38 (d, J=11.3 Hz, 1H), 2.54 (s, 3H), 2.73 (d, J=12.4 Hz, 1H), 2.86 (dd, J=7.7, 12.8 Hz, 1H), 3.22 (s, 3H), 7.28 (m, 3H), 7.39 (m, 2H). $^{13}$C NMR (75 MHz, CDCl$_3$) 22.8, 25.6, 28.2, 32.5, 42.4, 44.8, 45.7, 50.7, 61.3, 81.4, 127.9, 128.6, 129.9, 143.5. Mass spectrum (m/e) 249.0 (M+).

Example 1.50
(1S,2S)-(2-Methoxy-2-phenyl-cyclohexylmethyl)-dimethyl-amine HCl To a magnetically stirred solution of (1S,2S)-trifluoromethanesulfonic acid 3-(2-dimethylaminomethyl-1-methoxy-cyclohexyl)-phenyl ester (0.52 g, 1.31 mmol) in anhydrous DMF (2.63 mL) at room temperature under Ar atmosphere were added successively TEA (0.49 mL, 3.93 mmol), triphenylphosphine (13.7 mg, 0.052 mmol), Pd(OAc)$_2$ (5.9 mg, 0.0263 mmol), and formic acid (0.10 mL, 2.62 mmol). After stirring at 65° C. for 3 hours, the reaction was cooled to room temperature. Water (60 mL) was added, and the aqueous phase was extracted with EtOAc (2×100 mL). The combined organic layers were washed with water, dried (MgSO$_4$), and concentrated in vacuo to the crude product. The pure amine was obtained by column chromatography over silica gel (0.5:100 TEA/EtOAc as eluent) which gave the free base (0.255 g, 79%).

The HCl salt was prepared as follows. To a 50 mL RBF under argon was charged with (1S,2S)-(2-methoxy-2-phenyl-cyclohexylmethyl)-dimethyl-amine (0.255 g, 1.01 mmol). To the flask was added 5 mL of dry MTBE. 2N HCl (0.80 mL, 1.60 mmol) was added dropwise at room temperature. After stirring for 1 hour at room temperature, the white precipitate was filtered in vacuo to provide 0.24 g (82%) of HCl salt. $^1$H NMR (CDCl$_3$) 1.45–1.97 (m, 7H), 2.10 (s, 3H), 2.14 (m, 1H), 2.38 (d, J=11.3 Hz, 1H), 2.54 (s, 3H), 2.73 (d, J=12.4 Hz, 1H), 2.86 (dd, J=7.7, 12.8 Hz, 1H), 3.22 (s, 3H), 7.28 (m, 3H), 7.39 (m, 2H). $^{13}$C NMR (75 MHz, CDCl$_3$) 22.8, 25.6, 28.2, 32.5, 42.4, 44.8, 45.7, 50.7, 61.3, 81.4, 127.9, 128.6, 129.9, 143.5. Mass spectrum (m/e) 249.0 (M$^+$).

Example 1.51
(+/−)-3-(2-Dimethylaminomethyl-1-methoxy-cyclohexyl)-benzonitrile HCl To a magnetically stirred solution of (+/−)-trifluoromethanesulfonic acid 3-(2-dimethylaminomethyl-1-methoxy-cyclohexyl)-phenyl ester (0.60 g, 1.52 mmol) in anhydrous DMF (13.6 mL) at room temperature under Ar atmosphere were added successively tetrakis(triphenylphosphine)palladium(0) (1.74 g, 1.52 mmol) and zinc cyanide (0.106 g, 0.90 mmol). After stirring at 90° C. for 4 hours, the reaction was cooled to room temperature. Water (60 mL) was added, and the aqueous phase was extracted with EtOAc (2×100 mL). The combined organic layers were washed with water, dried (MgSO$_4$), and concentrated in vacuo to the crude product. The pure amine was obtained by column chromatography over silica gel (0.5:100 TEA/EtOAc as eluent) which gave the free base (0.35 g, 84%). $^1$H NMR (CDCl$_3$) 1.39–1.81 (m, 10H), 1.88 (s, 6H), 2.26 (dd, J=9.2, 12.0 Hz, 1H), 3.19 (s, 3H), 7.46 (d, J=7.6 Hz, 1H), 7.54 (m, 2H), 7.60 (m, 1H). $^{13}$C NMR (75 MHz, CDCl$_3$) 14.3, 21.8, 25.9, 27.0, 32.6, 45.7, 46.4, 50.3, 59.9, 60.4, 80.4, 112.1, 119.4, 128.9, 130.3, 130.5, 131.3, 146.0.

The HCl salt was prepared as follows. To a 50 mL RBF under argon was charged with (+/−)-3-(2-Dimethylaminomethyl-1-methoxy-cyclohexyl)-benzonitrile (0.25 g, 0.091 mmol). To the flask was added 5 mL of dry MTBE. 2N HCl (0.80 mL, 1.60 mmol) was added dropwise at room temperature. After stirring for 1 hour at room temperature, the white precipitate was filtered in vacuo to provide 0.196 g (70%) of HCl salt. $^1$H NMR (CD$_3$OD) 1.48–2.09 (m, 9H), 2.26 (s, 3H), 2.53 (m, 1H), 2.62 (s, 3H), 2.94 (m, 1H), 3.18 (s, 3H), 7.60 (m, 4H). $^{13}$C NMR (75 MHz, CDCl$_3$) 21.1, 24.8, 27.7, 31.9, 41.8, 43.9, 46.0, 50.4, 59.8, 79.7, 112.8, 118.7, 129.9, 130.0, 131.1, 131.2, 144.5. Mass spectrum (m/e) 274.5 (M$^+$).

Example 1.52
(+/−)-3-(1-Methoxy-2-methylaminomethyl-cyclohexyl)-benzonitrile HCl To a magnetically stirred solution of (+/−)-3-(2-dimethylaminomethyl-1-methoxy-cyclohexyl)-benzonitrile (0.10 g, 0.367 mmol) in anhydrous dichloroethane (2 mL) at room temperature under Ar atmosphere was added 1-chloroethyl chloroformate (0.059 mL, 0.825 mmol). After stirring at 100° C. for 2 hours, the reaction was concentrated in vacuo to a crude solid. MeOH (5 mL) was added and the reaction mixture was stirred at 90° C. for 2 hours. The reaction mixture was concentrated in vacuo to a crude oil. The pure amine was obtained by column chromatography over silica gel (0.5:100 TEA/EtOAc as eluent) which gave the free base (0.10 g, 94%). $^1$H NMR (CDCl$_3$) 1.64–2.09 (m, 11H), 2.17 (s, 3H), 2.33 (m, 1H), 3.16 (s, 3H), 7.47 (d, J=7.6 Hz, 1H), 7.55 (m, 2H), 7.61 (m, 1H). $^{13}$C NMR (75 MHz, CDCl$_3$) 21.6, 25.9, 26.6, 32.4, 36.7, 48.3, 50.3, 52.9, 80.7, 112.4, 119.2, 129.1, 130.3, 130.4, 131.1, 145.9.

The HCl salt was prepared as follows. To a 50 mL RBF under argon was charged with (+/−)-3-(1-Methoxy-2-methylaminomethyl-cyclohexyl)-benzonitrile (0.10 g, 0.038 mmol). To the flask was added 5 mL of dry MTBE. 2N HCl (0.38 mL, 0.76 mmol) was added dropwise at room temperature. After stirring for 1 hour at room temperature, the white precipitate was filtered in vacuo to provide 0.08 g (91%) of HCl salt. $^1$H NMR (CDCl$_3$) 1.23–2.09 (m, 14H), 2.82 (m, 1H), 3.22 (s, 3H), 7.59 (m, 4H). $^{13}$C NMR (75 MHz, CDCl$_3$) 21.4, 24.9, 26.1, 31.9, 34.1, 44.8, 50.5, 80.2, 112.9, 118.8, 129.8, 130.0, 131.1, 144.2. Mass spectrum (m/e) 260.2 (M$^+$).

Example 2
Binding and Uptake Assays

In vitro affinity for $\mu$, $\kappa$ and $\delta$ receptors, and particularly the $\mu$ receptor, is considered an indicator of in vivo analgesic activity. Several compounds of Formula I, including cis- and trans-OMT enantiomers, the N,N-didesmethyl analog of OMT, and ODMOMT were compared to tramadol and its O-desmethyl metabolite (ODMT), in binding assays for $\mu$, $\kappa$, and $\delta$ receptors. It has been reported that the analgesic effect of tramadol is due to interaction between the two enantiomers and the major metabolite, ODMT (Shipton, *Anaesth. Intensive Care*, 2000; 28, pp. 363–374). (ODMT is referred to as the M1 metabolite in some literature references.) In particular, the (R,R)-enantiomer of ODMT is believed to be responsible for the opioid component of the tramadol analgesic effect, based on its in vivo affinity for the $\mu$ receptor, which is much greater than that of either enantiomer of tramadol. (Gillen, et al., *Naunyn-Schmiedeberg's Arch Pharmacol*, 2000; 362; 116–121) Four other metabolites of tramadol have been identified, but none have been found to contribute to the analgesic activity of the parent compound (Id.).

The binding assays were performed using the following procedures:

| Receptor | Origin | Reference Compound | Bibliography |
|---|---|---|---|
| $\delta$ | Guinea-pig cerebral cortex | DPDPE | Cotton R., et al., Brit. J. Pharmacol, 84: 927–932(1985) |

-continued

| Receptor | Origin | Reference Compound | Bibliography |
|---|---|---|---|
| κ | Guinea-pig cerebellum | U 50488 | Kinouchi, K. & Pasternak, G. W., Eur. J. Pharmacol., 207: 135–141(1991) |
| μ | Rat cerebral cortex | DAMGO | Yoburn, B. C., et al., Eur. J. Pharmacol., 193: 105–108 (1991) |

Experimental conditions are summarized below:

| Receptor | Ligand | Conc. | Non-specific | Incubation |
|---|---|---|---|---|
| δ | [$^3$H]DPDPE | 1.5 nM | Naltrexone (10 μM) | 120 minutes/22° C. |
| κ | [$^3$H]U 69593 | 0.7 nM | Naloxone (10 μM) | 80 minutes/22° C. |
| μ | [$^3$H]DAMGO | 1 nM | Naloxone (1 μM) | 60 minutes/22° C. |

Following incubation, the membranes were rapidly filtered under vacuum through glass fiber filters (GF/B, Packard or Filtermat A, Wallac). The filters were then washed several times with an ice-cold buffer using a cell harvester (Packard or Tomtec). Bound radioactivity was measured with a scintillation counter (Topcount, Packard or Betaplate, Wallac) using a liquid scintillation cocktail (Microscint 0, Packard) or a solid scintillant (MeltiLex B/HS, Wallac).

Functional Monoamine Uptake

Tramadol, its O-desmethyl metabolite (ODMT) and/or selected analogs were evaluated in uptake assays for norepinephrine (NE), dopamine (DA) and 5-HT (serotonin), as listed in Table 1, using the following general procedure.

Radioactivity was determined with a scintillation counter (Topcount, Packard) using a liquid scintillation cocktail (Microscint 0, Packard).

Experimental Protocols

The compounds were tested first in each assay at 0.001 μM, 0.1 μM and 10 μM in a single determination. In the assays where they caused more than 50% inhibition at 10 μM, they were further tested at ten concentrations in duplicate to obtain full inhibition curves. In each experiment, the respective reference compound was tested at a minimum of seven concentrations in duplicate to obtain an inhibition curve in order to validate this experiment.

Analysis and Expression of Results

For binding assays, the specific radioligand binding to the receptors is defined as the difference between total binding and nonspecific binding determined in the presence of an excess of unlabelled ligand. Results are expressed as a percent of control values and as a percent inhibition of control values obtained in the presence of the test compounds.

IC$_{50}$ values (concentration causing a half-maximal inhibition of control values) and Hill coefficients (nH) were determined by non-linear regression analysis of the inhibition curves. These parameters were obtained by Hill equation curve fitting. For binding assays, the inhibition constants (K$_i$) were calculated from the Cheng Prusoff equation (K$_i$=IC$_{50}$/(1+L/K$_D$), where L=concentration of radioligand in the assay, and K$_D$=affinity of the radioligand for the receptor). The IC$_{50}$ values obtained for the reference compounds are within accepted limits of historic averages obtained ±0.5 log units. Results are shown in Table 1. Designations are the same as used above: ODMT is O-desmethyltramadol, OMT is O-methyl tramadol,

| Assay | Origin | Reference Compound | Bibliography |
|---|---|---|---|
| NE uptake | Rat hypothalamus | Protriptyline | Perovic, S. and Muller, W. E. G., Arzneimittelforschung Drug Res., 45,: 1145–1148 (1995) |
| DA uptake | Rat corpora striatum synaptosomes | GBR 12909 | Janowsky, A, et al., S. M. J. Neurochem. 46: 1272–1276 (1986) |
| 5 HT uptake | Rat brain synaptosomes | Imipramine | Perovic, S. and Muller, W. E. G., Arzneimittelforschung Drug Res., 45,: 1145–1148 (1995) |

Experimental conditions are summarized below:

| Assay | Tracer | Incubation | Reaction Process | Method of Detection |
|---|---|---|---|---|
| NE uptake | [$^3$H]NE (0.2 μCi/ml) | 20 min./37° C. | [$^3$H]NE incorporation into synaptosomes | Liquid scintillation |
| DA uptake | [$^3$H]DA (0.2 μCi/ml) | 15 min./37° C. | [$^3$H]DA incorporation into synaptosomes | Liquid scintillation |
| 5-HT uptake | [$^3$H]5-HT (0.2 μCi/ml) | 15 min./37 ° C. | [$^3$H]5-HT incorporation into synaptosomes | Liquid scintillation |

ODMOMT is O-desmethyl O-methyl tramadol, and NDMOMT is the di-N-desmethyl derivative of OMT.

TABLE 1

IC$_{50}$ Values for Tramadol (T) and Metabolites in Opioid Binding (nM) and Functional Monoamine Uptake Assays ($\mu$M)

| Compound Tested | $\mu$ | $\kappa$ | $\delta$ | NE | DA | 5-HT |
|---|---|---|---|---|---|---|
| (R,R/S,S)-Tramadol | 8,270 | | | | | 0.71 |
| (R,R/S,S)-Tramadol | 7,640 | | | 3.1 | | 0.83 |
| (R,R/S,S)-ODMT | 47 | 3,150 | 7,710 | | | 4.0 |
| (R,R)-ODMT | 21 | 1,610 | 4,530 | | | 3.3 |
| (S,S)-ODMT | 948 | | | 7.1 | | 4.4 |
| (R,R/S,S)-OMT | 7,870 | | | 0.029 | | .55 |
| (S,S)-OMT | | | | 16 | | 0.45 |
| (R,R)-ODMOMT | 30 | 427 | 2,850 | 6.8 | | 2.1 |
| (R,R/S,S)-ODMOMT | 56 | 789 | 4,920 | 0.12 | | 2.6 |
| (S,S)-ODMOMT | 566 | 2,440 | | 0.051 | | 5.0 |
| (R,S/S,R)-OMT | 3,290 | | | 0.56 | 7.6 | 0.29 |
| (R,S/S,R)-NDMOMT | | | | | | 16 |
| (R,R)-OMT | 7,670 | | | 4.0 | | 0.65 |
| DAMGO | 2.1/4.4 | | | | | |
| U50488 | | 0.82 | | | | |
| DPDPE | | | 3.2/4.5 | | | |
| Protriptyline | | | | 0.04/0.026 | | |
| GBR 12909 | | | | | 0.0041 | |
| Imipramine | | | | | | 0.0032 |

Affinity of (R,R)-ODMOMT, (S,S)-ODMOMT, and racemic ODMOMT for the $\mu$ receptor was comparable to the corresponding enantiomer/racemate of ODMT, and much greater than that of racemic tramadol. Even more surprisingly, affinity of the same ODMOMT enantiomers and of the racemate for the $\kappa$ and $\delta$ receptors was greater than that of the corresponding ODMT enantiomers and of the racemate, indicating that ODMOMT has utility as an analgesic.

The table also shows that racemic OMT and (S,S)- and racemic ODMOMT were more effective at blocking NE uptake than racemic tramadol or (S,S)-ODMT. Cis- and trans-isomers of OMT (racemic) and (R,R)- and (S,S)-OMT were more effective at blocking at 5-HT uptake than racemic tramadol, (R,R)- or (S,S)-ODMT or racemic ODMT. Given the implication of both opioid and monoaminergic systems in depressive disorders, it is concluded that the compounds of formula I have utility as antidepressants. In addition, inhibition of NE uptake has been associated with effective treatment of attention deficit disorders, and the experimental results show that the above compounds are useful for the treatment of ADD.

Example 3
Dosage Forms

Example 3.1
Lactose-Free Tablet Dosage Form

Table 2 provides the ingredients for a lactose-free tablet dosage form of a compound of formula I:

TABLE 2

| Component | Quantity per Tablet (mg) |
|---|---|
| O-Methyl tramadol | 75 |
| Microcrystalline cellulose | 125 |
| Talc | 5.0 |
| Water (per thousand tablets) | 30.0 mL * |
| Magnesium Stearate | 0.5 |

* The water evaporates during manufacture.

The active ingredient is blended with the cellulose until a uniform blend is formed. The smaller quantity of cornstarch is blended with a suitable quantity of water to form a corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous technique.

Example 3.2
Tablet Dosage Form

Another tablet dosage formulation suitable for use with the active ingredients of the invention is provided in Table 3.

TABLE 3

| | Quantity per Tablet (mg) | | |
|---|---|---|---|
| Component | Formula A | Formula B | Formula C |
| O-Methyl tramadol | 20 | 40 | 100 |
| Microcrystalline cellulose | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with cellulose, starch and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

In the claims:

1. A compound at formula I:

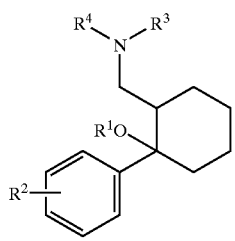

I wherein
- $R^1$ is selected from alkyl, aryl, alkylaryl, substituted alkyl, substituted aryl, and substituted alkylaryl;
- $R^2$ is selected from hydrogen, hydroxy, cyano, haloalkyl, glycosyl, $SO_2R^5$, and $OR^5$;
- $R^3$ and $R^4$ are independently selected from hydrogen and lower alkyl, or $R^3$ and $R^4$ taken together with nitrogen form a five- or six-membered heterocyclic or substituted heterocyclic ring; and
- $R^5$ is selected from alkyl, aryl, alkylaryl, substituted alkyl, substituted aryl, and substituted alkylaryl.

2. A compound according to claim 1, wherein $R^1$ is alkyl.
3. A compound according to claim 1, wherein $R^1$ is methyl, ethyl, n-propyl, n-butyl or n-cyclopropylethyl.
4. A compound according to claim 1, wherein $R^1$ is methyl.
5. A compound according to claim 1, wherein $R^2$ is hydroxy, cyano, $CH_2F$, $CHF_2$, $CF_3$, or $OR^5$.
6. A compound according to claim 1, wherein $R^2$ is hydroxy or $OR^5$.
7. A compound according to claim 1, wherein $R^2$ is methoxy.
8. A compound according to claim 1, wherein $R^2$ is hydroxy.
9. A compound according to claim 1, wherein $R^2$ is cyano.
10. A compound according to claim 1, wherein $R^3$ and $R^4$ are each methyl.
11. A cis-isomer of a compound according to claim 1.
12. A cis-isomer of a compound according to claim 1, enriched to any degree in either enantiomer.
13. An (R,R)-isomer of a compound according to claim 1.
14. An (S,S)-isomer of a compound according to claim 1.
15. A trans-isomer of a compound according to claim 1.
16. A trans-isomer of a compound according to claim 1, enriched to any degree in either enantiomer.
17. An (R,S)-isomer of a compound according to claim 1.
18. An (S,R)-isomer of a compound according to claim 1.
19. A compound according to claim 1, wherein $R^1$, $R^3$, and $R^4$ are each methyl, and $R^2$ is methoxy.
20. A cis-isomer of a compound according to claim 19.
21. An (R,R)-isomer of a compound according to claim 19.
22. An (S,S)-isomer of a compound according to claim 19.
23. A trans-isomer of a compound according to claim 19.
24. A compound according to claim 1, wherein $R^1$, $R^3$, and $R^4$ are each methyl, and $R^2$ is hydroxy.
25. A cis-isomer of a compound according to claim 24.
26. An (R,R)-isomer of a compound according to claim 24.
27. An (S,S)-isomer of a compound according to claim 24.
28. A trans-isomer of a compound according to claim 24.
29. An (R,S)-isomer of a compound according to claim 24.

30. A compound according to claim 1, wherein $R^1$ and $R^4$ are each methyl, $R^2$ is methoxy and $R^3$ is hydrogen.
31. A compound according to claim 1, wherein $R^1$ is methyl, $R^2$ is methoxy and $R^3$ and $R^4$ are each hydrogen.
32. A compound according to claim 1, selected from

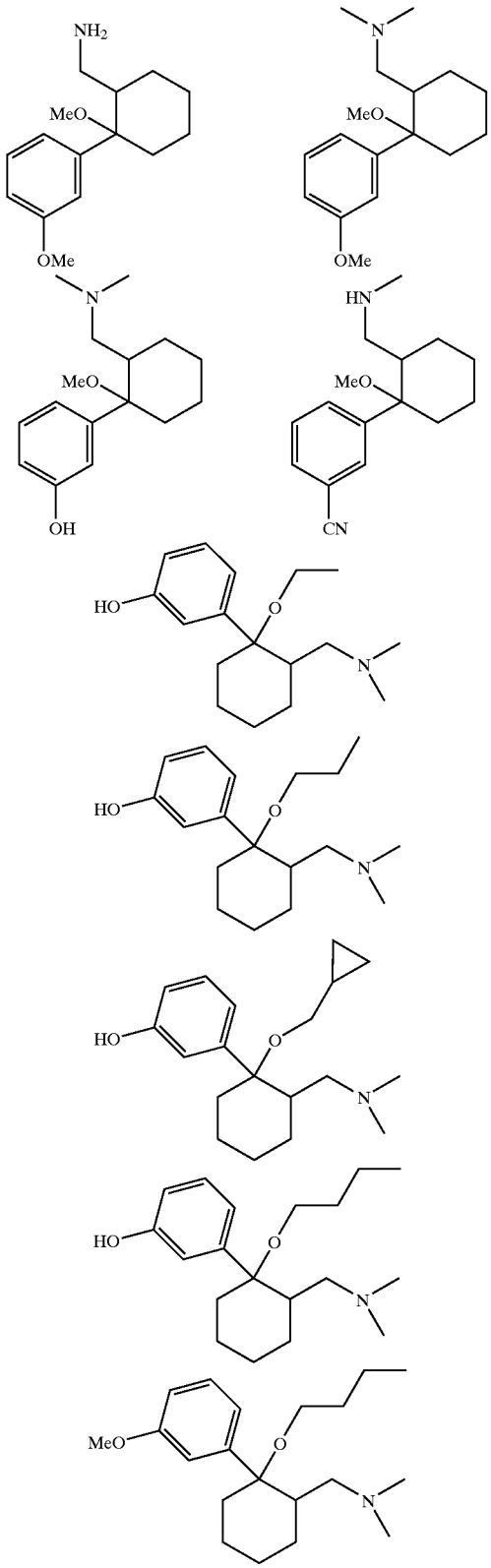

-continued

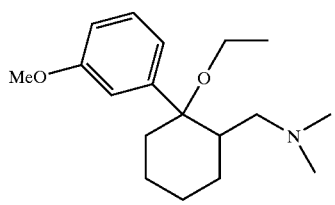

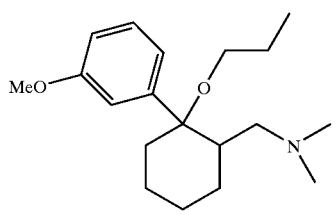

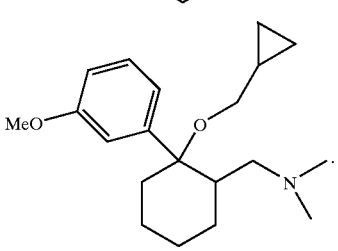

33. A compound according to claim 1, having the formula

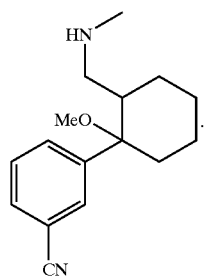

34. A compound according to claim 1, having the formula

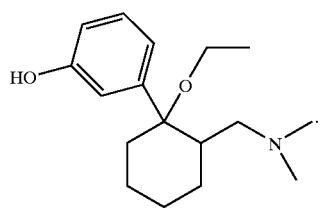

35. A compound according to claim 1, having the formula

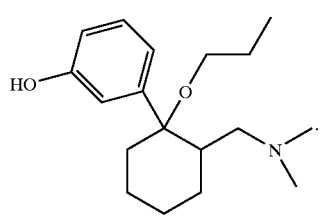

36. A compound according to claim 1, having the formula

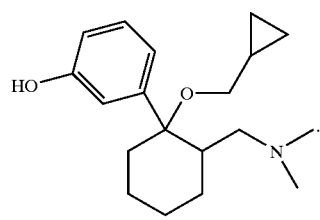

37. A compound according to claim 1, having the formula

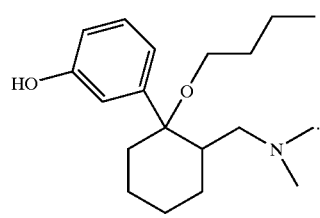

38. A compound according to claim 1, having the formula

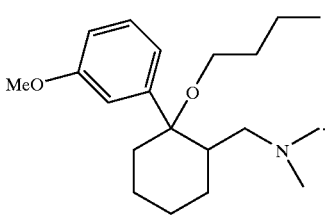

39. A compound according to claim 1, having the formula

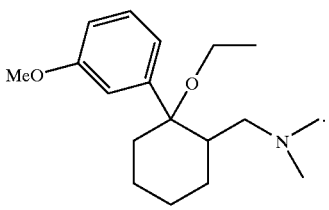

40. A compound according to claim 1, having the formula

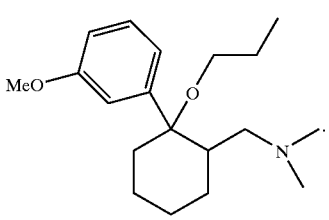

41. A compound according to claim 1, having the formula

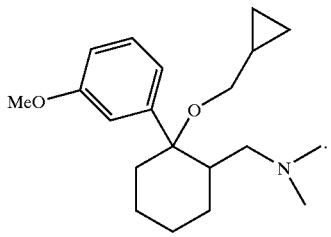

42. A method for treating disorders modulated by at least one of opiate receptor activity and monoamine activity, said method comprising administering to a mammal in need thereof a therapeutically effective amount of a compound according to claim 1, or a pharmaceutically acceptable salt thereof.

43. A method according to claim 42, wherein said compound of claim 1 is O-methyl tramadol.

44. A method according to claim 42, wherein said compound of claim 1 is O-desnethyl O-methyl tramadol.

45. A method for relieving acute and chronic pain, said method comprising administering to a mammal in need thereof a therapeutically effective amount of a compound according to claim 1, or a pharmaceutically acceptable salt thereof.

46. A method according to claim 45, wherein said compound of claim 1 is O-methyl tramadol.

47. A method according to claim 45, wherein said compound of claim 1 is O-desmethyl O-methyl tramadol.

48. A method for treating affective disorders, said method comprising administering to a mammal in need thereof a therapeutically effective amount of a compound according to claim 1, or a pharmaceutically acceptable salt thereof.

49. A method according to claim 48, wherein said compound of claim 1 is O-methyl tramadol.

50. A method according to claim 48, wherein said compound of claim 1 is O-desmethyl O-methyl tramadol.

51. A method for treating an attention deficit disorder, said method comprising administering to a mammal in need thereof a therapeutically effective amount of a compound according to claim 1, or a pharmaceutically acceptable salt thereof.

52. A method according to claim 51, wherein said compound of claim 1 is O-methyl tramadol.

53. A method according to claim 51, wherein said compound of claim 1 is O-desmethyl O-methyl tramadol.

54. A pharmaceutical composition comprising a compound of formula I, or a pharmaceutically acceptable salt thereof:

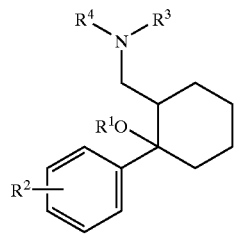

I wherein $R^1$ is selected from alkyl, aryl, alkylaryl, substituted alkyl, substituted aryl, and substituted alkylaryl;

$R^2$ is selected from hydrogen, hydroxy, cyano, haloalkyl, glycosyl, $SO_2R^5$, and $OR^5$;

$R^3$ and $R^4$ are independently selected from hydrogen and lower alkyl, or $R^3$ and $R^4$ taken together with nitrogen form a five- or six-membered heterocyclic or substituted heterocyclic ring; and $R^5$ is selected from alkyl, aryl, alkylaryl, substituted alkyl, substituted aryl, and substituted alkylaryl.

55. A pharmaceutical composition according to claim 54, additionally comprising a pharmaceutically acceptable carrier.

56. A pharmaceutical composition according to claim 54, adapted for oral administration.

57. A pharmaceutical composition according to claim 56, in the form of a tablet or capsule.

58. A pharmaceutical composition according to claim 54, adapted for sustained release delivery of the compound of formula I.

59. A pharmaceutical composition according to claim 54, additionally comprising an amount of the compound of formula I ringing from 10 mg to 1000 mg.

60. A pharmaceutical composition according to claim 54, wherein $R^1$, $R^3$, and $R^4$ are each methyl, and $R^2$ is methoxy.

61. A pharmaceutical composition according to claim 54, wherein $R^1$, $R^3$, and $R^4$ are each methyl, and $R^2$ is hydroxy.

* * * * *

UNITED STATES PATENT AND TRADEMARK OFFICE
CERTIFICATE OF CORRECTION

PATENT NO. : 6,780,891 B2
DATED : August 24, 2004
INVENTOR(S) : Senanayake et al.

It is certified that error appears in the above-identified patent and that said Letters Patent is hereby corrected as shown below:

Title page,
Item [75], Inventors, delete the word "Wellesly" and insert -- Wellesley --

Column 50,
Line 41, delete the word "ringing" and insert -- ranging --

Signed and Sealed this

Fourteenth Day of December, 2004

JON W. DUDAS
*Director of the United States Patent and Trademark Office*